(12) United States Patent
Kennedy et al.

(10) Patent No.: US 11,504,369 B2
(45) Date of Patent: Nov. 22, 2022

(54) CYTOSINE-BASED TET ENZYME INHIBITORS

(71) Applicant: President and Trustees of Bates College, Lewiston, ME (US)

(72) Inventors: Andrew Kennedy, Lewiston, ME (US); Gabriella N. L. Chua, San Francisco, CA (US); Kelly L. Wassarman, Brighton, MA (US); Haoyu Sun, Beijing (CN)

(73) Assignee: President and Trustees of Bates College, Lewiston, ME (US)

( * ) Notice: Subject to any disclaimer, the term of this patent is extended or adjusted under 35 U.S.C. 154(b) by 0 days.

(21) Appl. No.: 16/825,324

(22) Filed: Mar. 20, 2020

(65) Prior Publication Data

US 2020/0316069 A1 Oct. 8, 2020

Related U.S. Application Data

(60) Provisional application No. 62/822,774, filed on Mar. 22, 2019.

(51) Int. Cl.
*A61K 31/513* (2006.01)
(52) U.S. Cl.
CPC .................. *A61K 31/513* (2013.01)
(58) Field of Classification Search
CPC .................. C07D 239/36; A61K 31/513
See application file for complete search history.

(56) References Cited

U.S. PATENT DOCUMENTS 8,916,579 B2 * 12/2014 Boebel .................. A01N 47/36
514/274
2012/0322755 A1 12/2012 Barciszewski et al.

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
PubChem CID 424790, 7 pages (2005).*
PubChem CID 424494, 7 pages (2005).*
PubChem CID 11701450, 13 pages (2006).*
PubChem CID 11492131, 8 pages (2006).*
PubChem CID 10773925, 13 pages (2006).*
PubChem CID 71742583, 10 pages (2013).*
PubChem CID 102010270, 7 pages (2015).*
PubChem CID 134389283, 7 pages (2018).*
PubChem CID 14632492, 8 pages (2007).*
PubChem CID 21793030, 7 pages (2007).*
PubChem CID 20587503, 8 pages (2007).*
Chua et al., Cytosine-Based TET Enzyme Inhibitors, ACS Medicinal Chemistry Letters, vol. 10, pp. 180-185 (Jan. 31, 2019).*
Valiante et al., CAPLUS Abstract 144:108349 (2006).*
Medebielle et al., CAPLUS Abstract 123:256554 (1995).*
PubChem CID 129695566, 9 pages (2017).*
PubChem CID 44144264, 9 pages (2009).*
PubChem CID 379361, 9 pages (2005).*
International Search Report and Written Opinion for Application No. PCT/US2019/023760 dated May 28, 2019.
[No Author Listed] PubChem CID 597. Sep. 16, 2004. pp. 1-30. Retrieved from the Internet at https://pubchem.ncbi.nlm.nih.gov/compound/597>.
[No Author Listed] PubChem CID 3366. March Mar. 25, 2005. pp. 1-74. Retrieved from the Internet at https://pubchem.ncbi.nlm.nih.gov/compound/3366>.
[No Author Listed] PubChem CID 65040. Mar. 26, 2005. pp. 1-24. Retrieved from the Internet at https://pubchem.ncbi.nlm.nih .gov/compound/65040>.
Gjoneska et al., Conserved Epigenomic Signals in Mice and Humans Reveal Immune Basis of Alzheimer's Disease. Nature. Feb. 19, 2015;518(7539):365-9. doi: 10.1038/nature14252.
Kennedy et al., Tcf4 Regulates Synaptic Plasticity, DNA Methylation, and Memory Function. Cell Rep. Sep. 6, 2016;16(10):2666-2685. doi: 10.1016/j.celrep.2016.08.004. Epub Aug. 25, 2016.
Stefanelli et al., Learning and Age-Related Changes in Genomewide H2A.Z Binding in the Mouse Hippocampus. Cell Rep. Jan. 30, 2018;22(5):1124-1131. doi: 10.1016/j.celrep.2018.01.020.

* cited by examiner

*Primary Examiner* — Deepak R Rao
(74) *Attorney, Agent, or Firm* — Wolf, Greenfield & Sacks, P.C.

(57) ABSTRACT

Provided herein, in some embodiments, are cytosine analogs, compositions comprising cytosine analogs, and methods of use for inhibiting a Ten-eleven translocation (TET) enzyme.

13 Claims, 13 Drawing Sheets

| Chain | |
|---|---|
| hTet2 | GGSDFPSCRQVEQIIEKDEGPFYTRLGAGPNVAAIREIMEERFGQKGKAIRIERVIYTGKEGKSSQGCPIAKWVRKSSSEEKLL |
| 2:hTet1 | KDSELPTCSCLDRVIQRDKGPYYTHLGAGPSVAAVREIMENRYGQKGNAIRIEIVVYTGKEGKSSBGCPIAKWVLRRSSBEEKVL |
| Chain | |
| hTet2 | CLVREBAGHTCEAAVIVILILVWEGIPLSLADKLYSELTETLRKY-GTLTNRRCALNEERTCACQGLDPETCGASFSFGCSWSMY |
| 2:hTet1 | CLVRQNTGHHCPTAVNVVLINVWDGIPLPMADRLYTELTENLKSYNGHPTDRRCTLNENRTCTCQGIDPETCGASFSFGCSWSMY |
| Chain | |
| hTet2 | YNGCKFARSKIPRKFKLLGDDPKEEEKLESHLQNLSTLMAPTYKRLAPDAYNNQIEYEHRAPECRLGLKEGRPFSGVTACLDFCA |
| 2:hTet1 | FNGCKFGRSPSPRRPRIDPSSPLHEEKNLEDNLQSLATRLAPIYKQYAPVAYQNQVEYENVARECRLGSKEGRPFSGVTACLDFCA |
| Chain | |
| hTet2 | HAHRDLHNMQNGSTLVCTLTREDNREFGGKPEDEQLHVLPLYKVSDVDEFGSVEAQEEKKRSGAIQVLSSFRRKVRMLAEPVKTC |
| 2:hTet1 | HPHRDIHNMNNGSTVVCTLTREDNRSLCVIPQDEQLHVLPLYKLSDTDEFGSKEGMEAKIKSGAIEVLAPRKKKRTCFTQPVPRS |
| Chain | |
| hTet2 | RQRK······LEAKKAAAEK············································· |
| 2:hTet1 | GKKKAAMMTEVLAHKIRAVEKKPIPRIRRKNSTTTNNSKFSSLPTLGSNTETVQFEVKSETEPHFILKSSDNTKTYSLMPSAPH |
| Chain | |
| hTet2 | ················································LSGGGGSGGGGSGGGGS··················· |
| 2:hTet1 | FVKEASPGFSWSPKTASATPAPLKNDATASCGFGERSSTPHCTMPSGRLSGANAAAADGPGISQLGEVAPLPTLSAPVMEPLINS |
| Chain | |
| hTet2 | ·········································DEVWSDSEQSFLDPDIGGV |
| 2:hTet1 | EPSTGVTEPLTPHQPNHQPSFLTSPQDLASSPMEEDEQHSEADEPPSDEPLSDDPLSPAEEKLPHIDEYWSDSEHIFLDANIGGV |
| Chain | |
| hTet2 | AVAPTHGSILIECAKRELHATTPLKNPNRNHPTRISLVFYQRKSMNEPKHGLALWEAKM-AEKAREKEEECERYG |
| 2:hTet1 | AIAPAHGSVLIECARRELHATTPVEHPNKNHPTKLSLVFYQRKNLNKFQHGFELNKIKFEAKEAKNKKMKASEQK |

FIG. 5A

CYTOSINE-BASED TET ENZYME INHIBITORS

RELATED APPLICATIONS

This application claims the benefit of priority under 35 U.S.C. § 119 of U.S. provisional application 62/822,774, filed Mar. 22, 2019, the entire contents of which are incorporated herein by reference.

GOVERNMENT SUPPORT

This invention was made with government support under GM103423 awarded by National Institutes of Health. The government has certain rights in the invention.

BACKGROUND OF THE INVENTION

DNA methylation is a dynamic process in which the methylation state of the genome changes during cellular transitions, such as differentiation and altered neuronal plasticity, and becomes dysregulated in disease states, such as cancer. Ten-eleven translocation methylcytosine dioxygenase (TET) enzymes catalyze the reverse process of DNA demethylation by recognizing 5-methylcytosine and oxidizing the methyl group via an Fe(II)/alpha-ketoglutarate-dependent mechanism.

SUMMARY OF THE INVENTION

The present disclosure is based, at least in part, on the discovery that cytosine-based compounds, such as 1-([1,1'-biphenyl]-3-yl)-4-amino-5-chloropyrimidin-2(1H)-one (Bobcat339), effectively inhibited the oxidation of methylated DNA by TET enzymes. As such, compositions containing cytosine-based compounds would benefit studies and treatment of disease associated with dysregulated DNA methylation.

Accordingly, one aspect of the present disclosure provides a cytosine analog of formula I

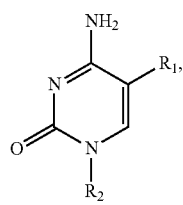

I or a pharmaceutically acceptable salt thereof,
wherein $R_1$ is independently selected from the group consisting of hydrogen, halogen, optionally substituted alkyl, optionally substituted alkenyl, or optionally substituted alkynyl, and
wherein $R_2$ is selected from the group consisting of hydrogen, optionally substituted carbocyclyl, optionally substituted heterocyclyl, optionally substituted aryl, or optionally substituted heteroaryl.

In some embodiments of any one of the compositions or methods provided herein, $R_1$ is hydrogen. In some embodiments of any one of the compositions or methods provided herein, $R_1$ is halogen. In some embodiments of any one of the compositions or methods provided herein, $R_1$ is optionally substituted $C_{1-6}$ alkyl. In some embodiments of any one of the compositions or methods provided herein, $R_1$ is —Cl or —$CF_3$.

In some embodiments of any one of the compositions or methods provided herein, $R_2$ is hydrogen. In some embodiments of any one of the compositions or methods provided herein, $R_2$ is optionally substituted $C_{1-6}$ alkyl. In some embodiments of any one of the compositions or methods provided herein, $R_2$ is of formula —$(CH_2)_nC(=O)N(R^4)_2$, wherein:

n is 1, 2, or 3; and each instance of $R^4$ is independently hydrogen, optionally substituted $C_{1-6}$ alkyl, or optionally substituted aryl.

In some embodiments of any one of the compositions or methods provided herein, $R_2$ is of formula:

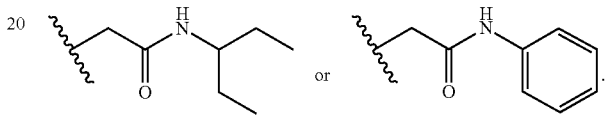

In some embodiments of any one of the compositions or methods provided herein, $R_2$ is optionally substituted phenyl or optionally substituted napthyl. In some embodiments of any one of the compositions or methods provided herein, $R_2$ is phenyl optionally substituted with halogen, optionally substituted $C_{1-6}$ alkyl, or optionally substituted phenyl. In some embodiments of any one of the compositions or methods provided herein, $R_2$ is unsubstituted phenyl, 4-chlorophenyl, 3-chlorophenyl, 2-biphenyl, 3-biphenyl, 4-biphenyl, 4-methylphenyl, 1-napthyl, or 2-napthyl. In some embodiments of any one of the compositions or methods provided herein, $R_2$ is optionally substituted heteroaryl. In some embodiments of any one of the compositions or methods provided herein, $R_2$ is optionally substituted pyridyl, optionally substituted quinolyl, optionally substituted dibenzofuranyl, or optionally substituted benzo[d]oxazolyl. In some embodiments of any one of the compositions or methods provided herein, $R_2$ is nicotinonitrile, 5-methoxypyridin-2-yl, 4-dibenzofuranyl, or unsubstituted 3-quinolinyl, 2-phenylbenzo[d]oxazol-6-yl, or 2-phenylbenzo[d]oxazol-7-yl.

In some embodiments of any one of the compositions or methods provided herein, the cytosine analog of formula I is selected from the group consisting of

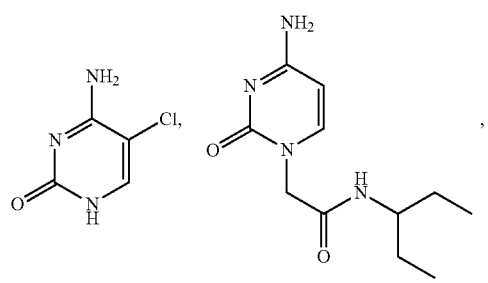

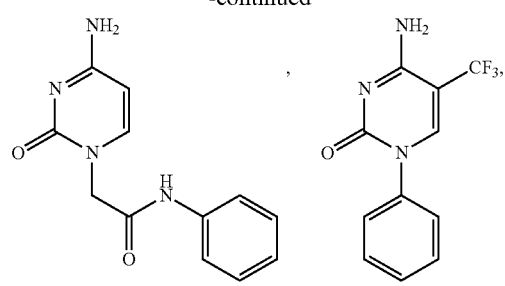
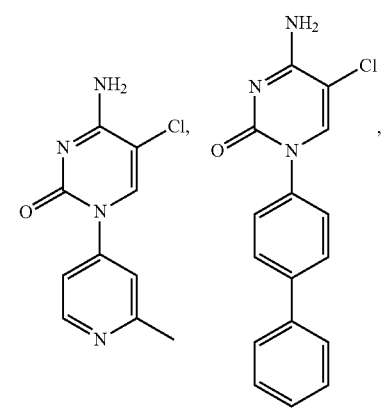
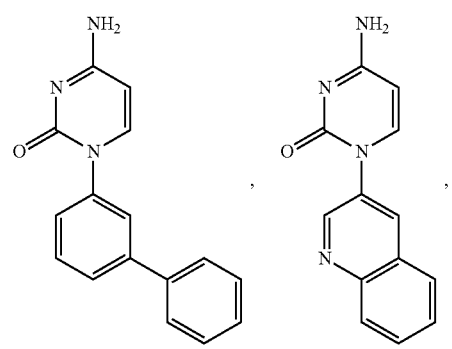
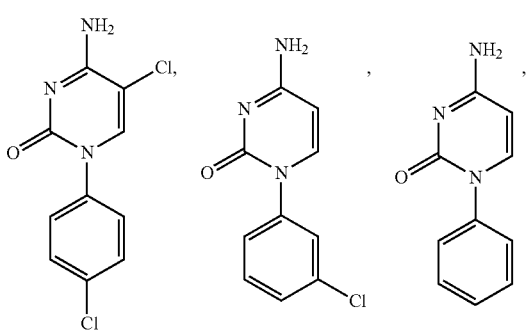
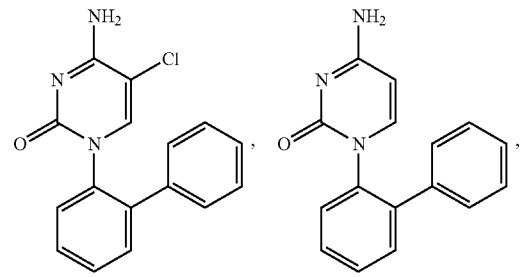
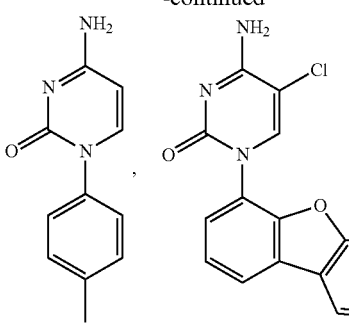
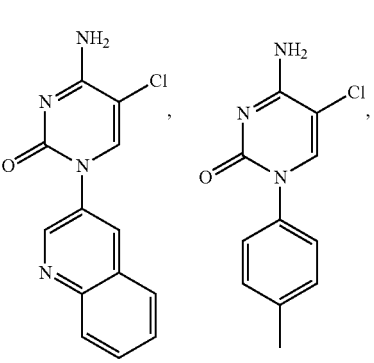
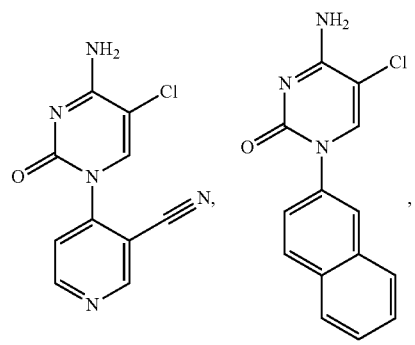
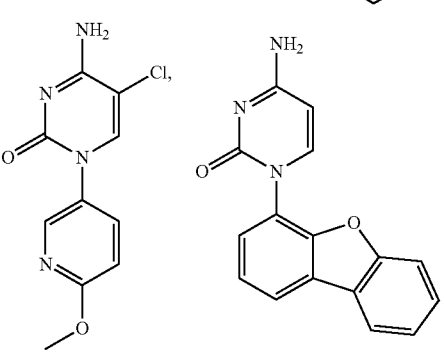

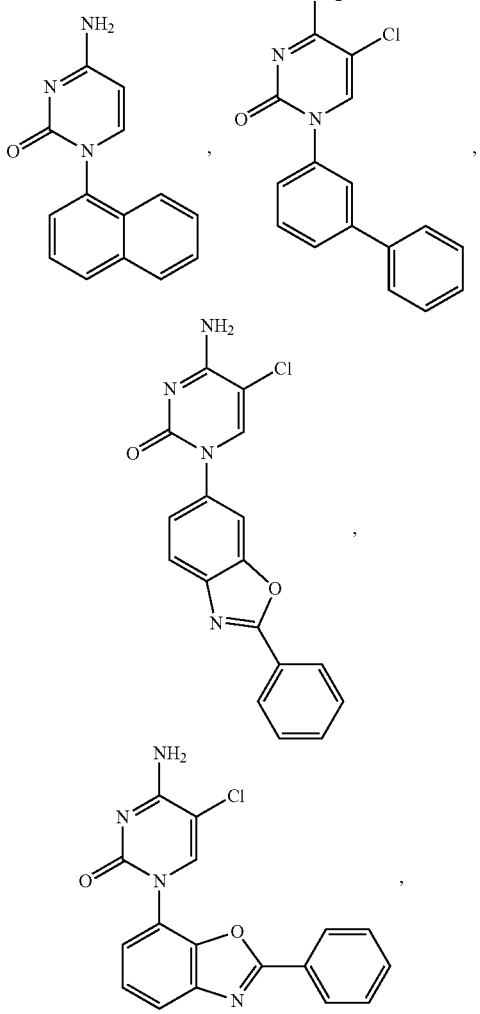

and a pharmaceutically acceptable salt of any one of the aforementioned compounds.

Another aspect of the present disclosure provides a method for inhibiting a Ten-eleven translocation (TET) enzyme, the method comprising contacting any one of the cytosine analogs described herein with the TET enzyme. In some embodiments of any one of the compositions or methods provided herein, the TET enzyme is selected from the group consisting of TET1, TET2, and TET3.

In some embodiments of any one of the compositions or methods provided herein, the contacting occurs in vitro or in vivo. In some embodiments of any one of the compositions or methods provided herein, the contacting occurs in a cell. In some embodiments of any one of the compositions or methods provided herein, the cell is in a subject. In some embodiments of any one of the compositions or methods provided herein, the contacting occurs through administration to the subject.

In yet another aspect, the present disclosure provides a method for inhibiting a Ten-eleven translocation (TET) enzyme in a subject, the method comprising administering to the subject a therapeutically effective amount of any one of the cytosine analogs described herein.

In some embodiments of any one of the methods provided herein, the subject is a human having or at risk for having a condition characterized by defective DNA methylation and/or increased TET enzyme activity. The condition is any one of the conditions described herein.

The details of several embodiments of the invention are set forth in the accompanying Figures and the Detailed Description. Other features, objects, and advantages of the invention will be apparent from the description and from the claims.

DETAILED DESCRIPTION OF THE DRAWINGS

Various aspects and embodiments will be described with reference to the following figures.

FIG. 1 is a graph showing results from testing methyl bioisosteres at the $R_1$ position for TET inhibition. Chloro, bromo, and trifluoromethyl-substituted derivatives were tested for inhibition of TET1 or TET2-mediated oxidation of methylated dsDNA. Each compound was tested at 100 μM in an ELISA. All data presented are N=3, error bars indicate+/−sem. Two-way ANOVA, *P<0.05, P<0.01, *P<0.001.

FIG. 2A is a graph showing results from testing several aryl groups at the $R_2$ position for TET inhibition. Each compound was tested at 100 μM in an ELISA. 3-biphenyl substitution significantly increased TET1 inhibition (P=0.002) over simple phenyl substitution, while 2-biphenyl (P=0.0001) and 4-biphenyl (P<0.0001) substitution significantly reduced TET1 inhibition as compared to a phenyl substitution. All data presented are N=3, error bars indicate+/−sem.

Figure 4:
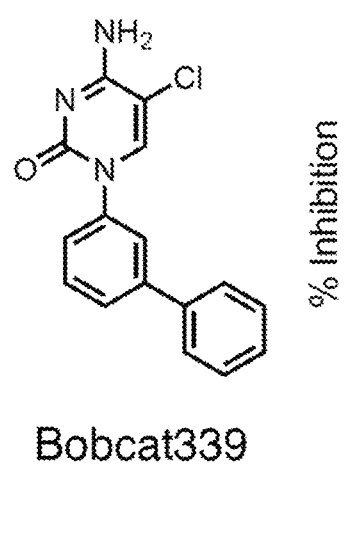

FIG. 4 is a graph showing results from testing the specificity of Bobcat339 for TET and DNMT3a enzymes. Bobcat339 inhibits TET1 (IC50=33 μM) and TET2 (IC50=73 μM), but not DNMT3a. All data presented are N=3, error bars indicate+/−sem.

FIG. 5A is an image showing sequence alignment of TET1 and TET2.

Figure 5B:
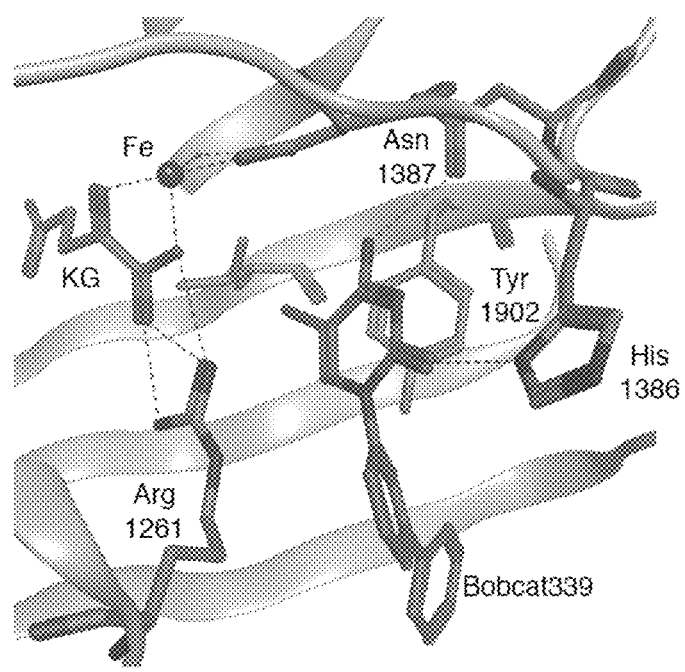

FIG. 5B is an image showing Bobcat339 docked into a homology model of TET1.

Figure 5C:
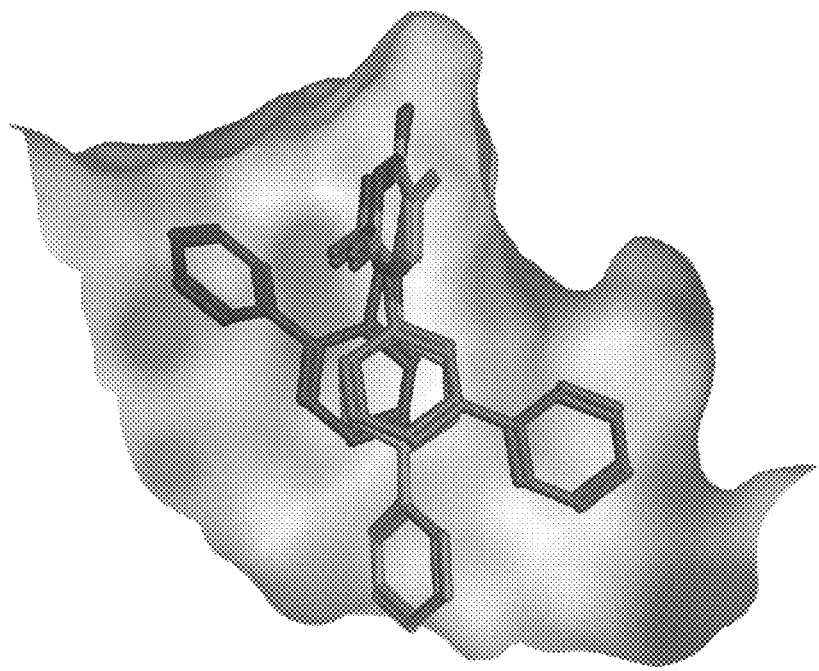

FIG. 5C is an image showing the predicted binding conformations of Bobcat339, its 2-biphenyl isomer, and its 4-biphenyl isomer.

Figure 6A:
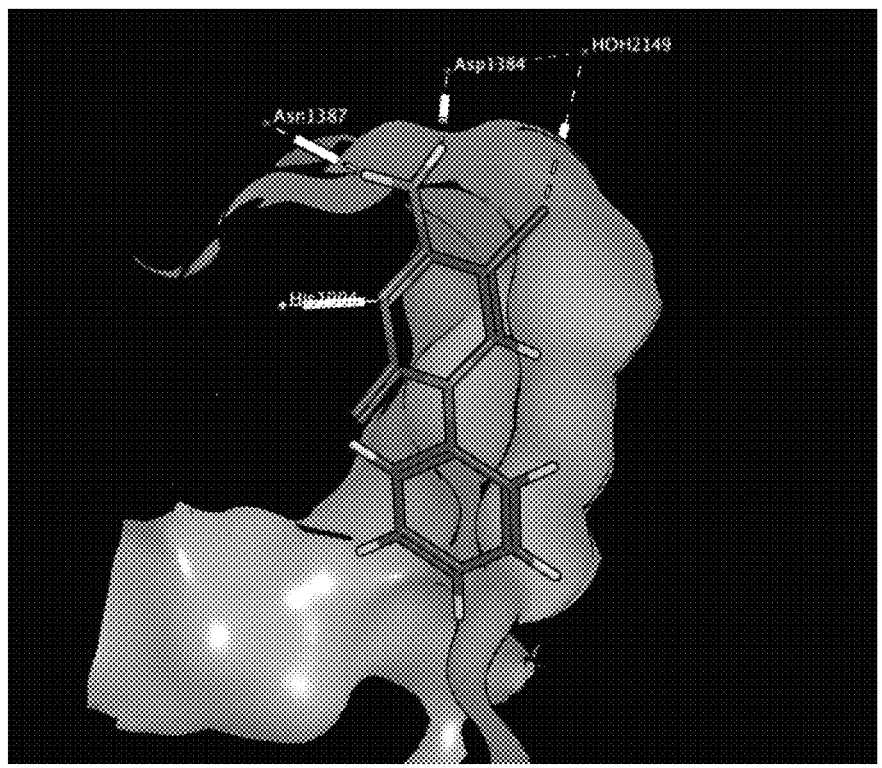

FIG. 6A is an image showing KW1019 (Bobcat216) docked to TET2.

Figure 6B:
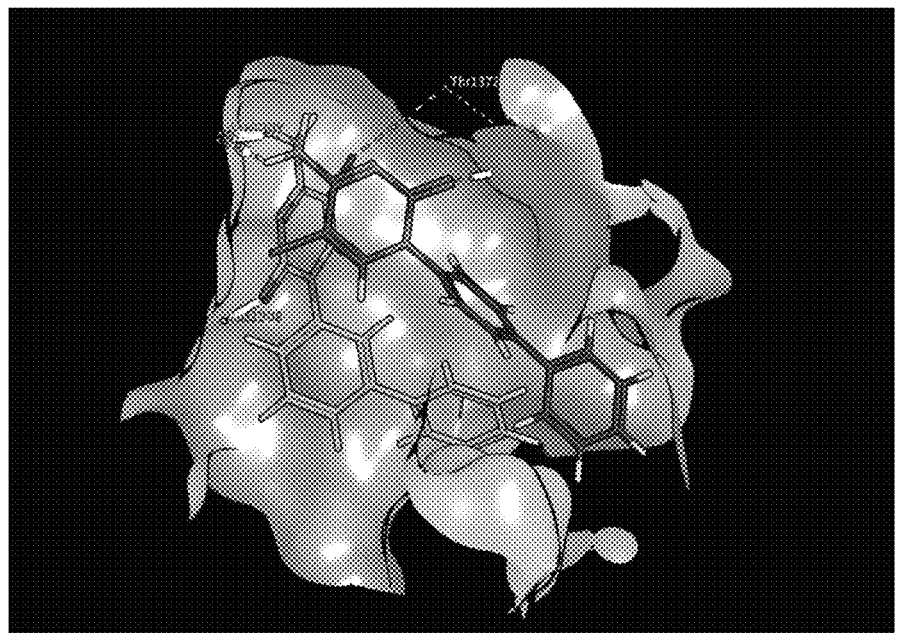

FIG. 6B is an image showing KW1019 (Bobcat216) and HS1039 docked to TET2.

Figure 6C:
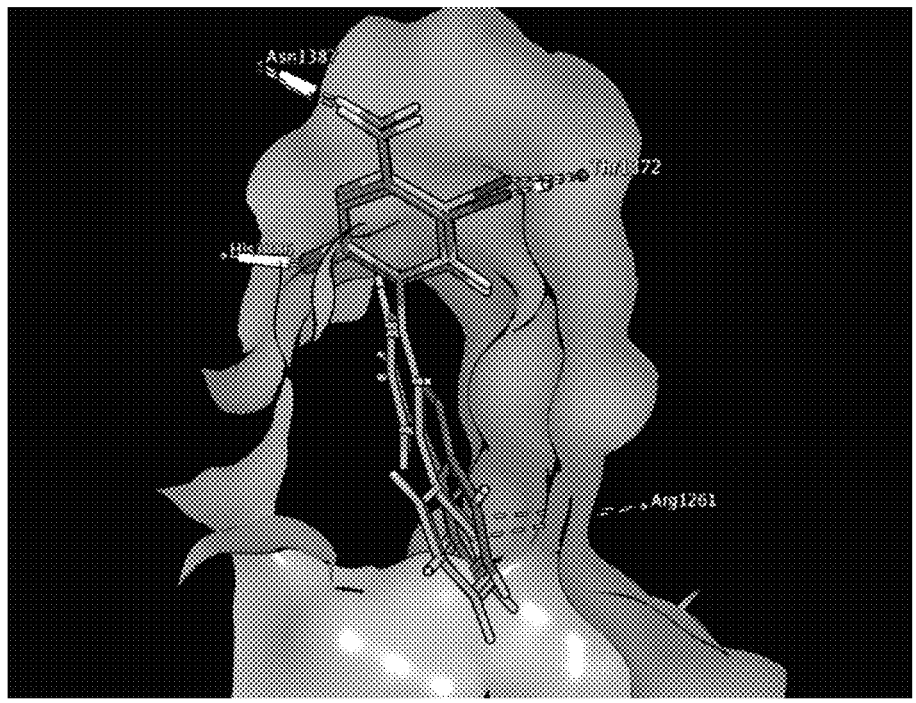

FIG. 6C is an image showing HS1039 and HS1041 docked to TET2.

Figure 6D:
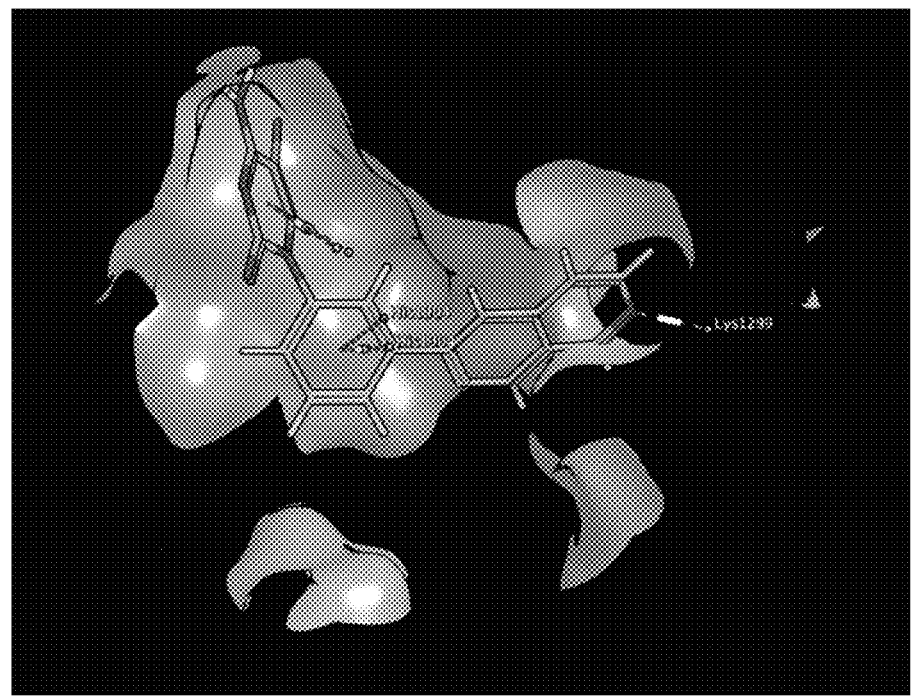

FIG. 6D is an image showing that predicted binding energies were higher for molecules with larger $R_2$ groups due to the greater number of favorable contacts being made with TET2.

Figure 7A:
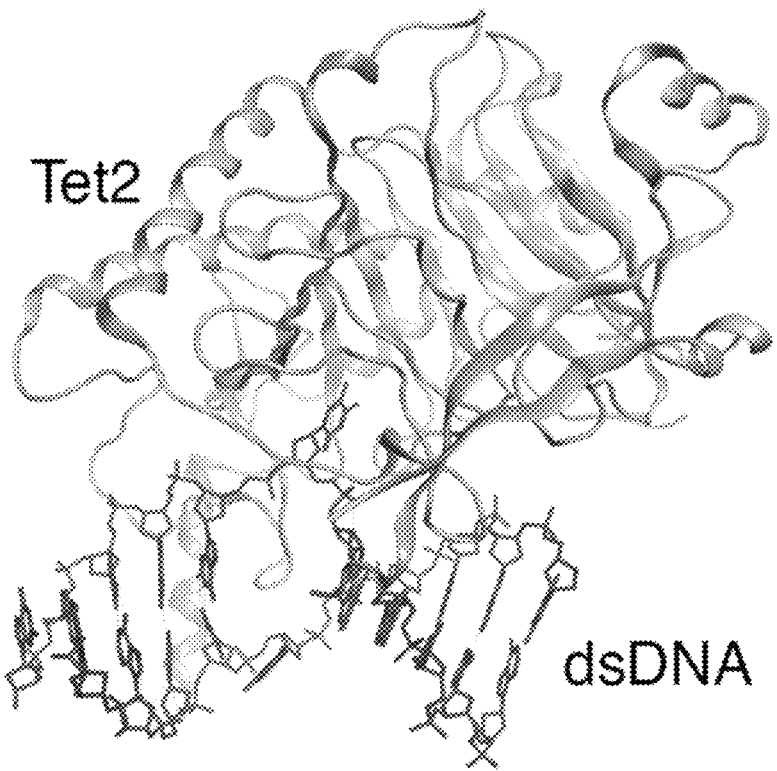

FIG. 7A is an image showing the crystal structure of TET2-DNA complex. TET2 binds dsDNA, breaks the double helix, and inserts 5mC into its active site. Blue=basic residue, red=acidic residue, and black=neutral residue.

Figure 7B:
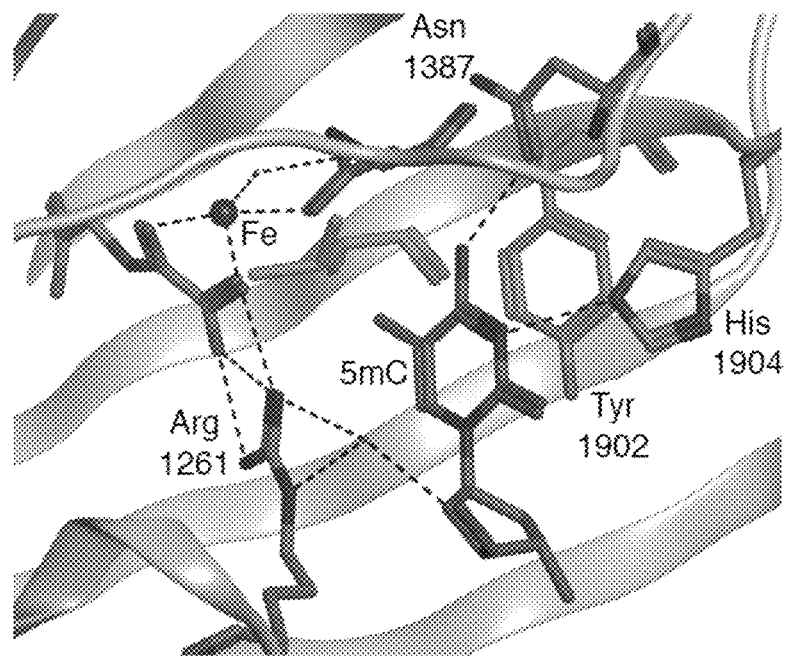

FIG. 7B is an image showing a view of the TET2 active site binding 5mC by forming hydrogen bonds with Asn1387, His1904, and Arg1261, all of which are residues for TET2 catalytic activity and methylated DNA binding. The oxidative iron center is shown in proximity to the methyl group on 5mC. Blue=basic residue, red=acidic residue, and black=neutral residue.

Figure 7C:
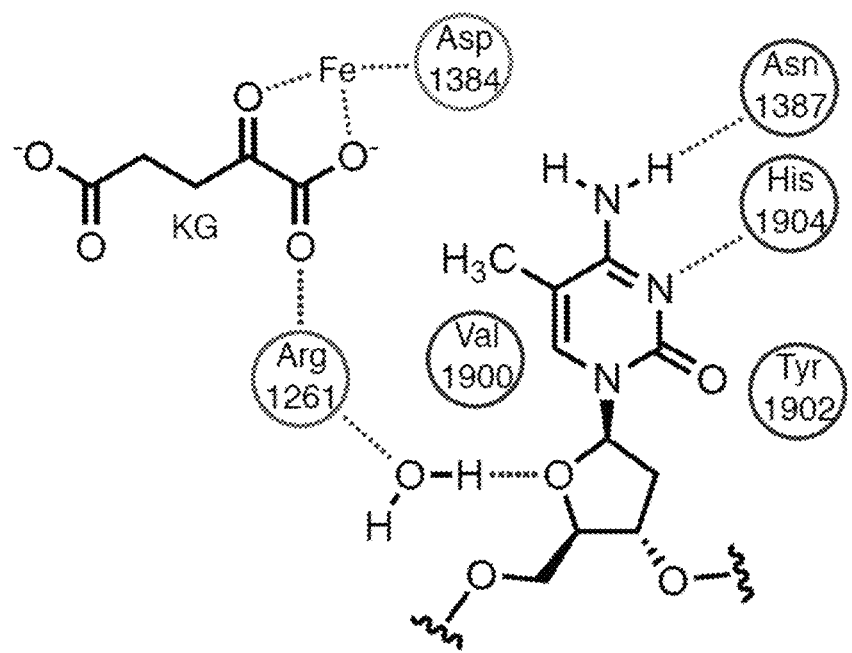

FIG. 7C is an image showing a 2D rendering of the 5mC-bound TET2 active site and residue interactions. Blue=basic residue, red=acidic residue, and black=neutral residue.

Figure 8:
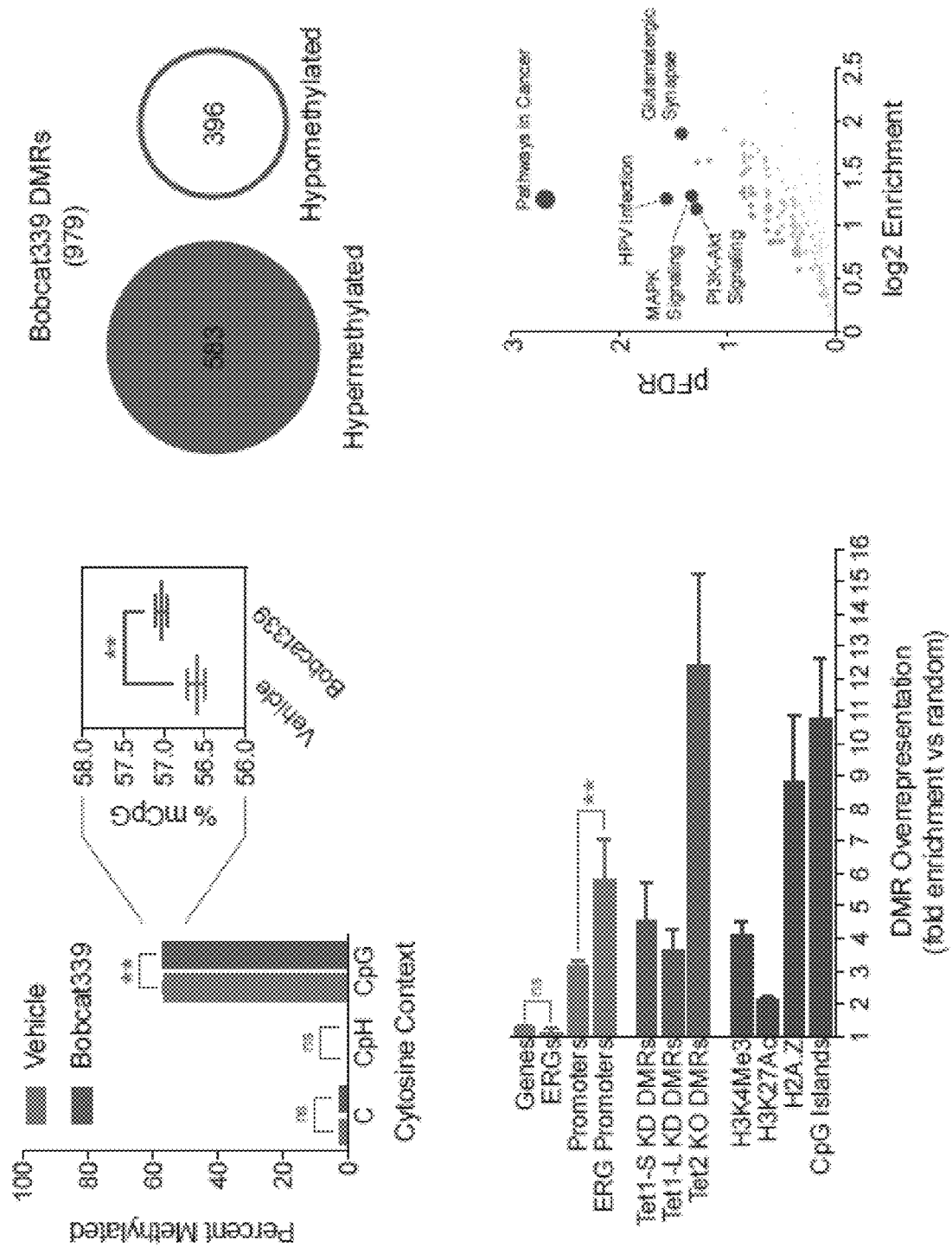

FIG. 8 shows results from an analysis of DNA methylation performed with whole genome bisulfite sequencing in HT22 cells.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⌇ is a single bond where the stereochemistry of the moieties immediately attached thereto is not specified, --- is absent or a single bond, and ═══ or ═══ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., $CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., $CH_2F$, $CHF_2$, $CF_3$ or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include $CF_3$, $CF_2CF_3$, $CF_2CF_2CF_3$, $CCl_3$, $CFCl_2$, $CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2 butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., CH=CHCH$_3$,

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl").

The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a nonaromatic cyclic hydrocarbon group having from 3 to 14 ring carbon atoms ("$C_{3-14}$ carbocyclyl") and zero heteroatoms in the nonaromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3 to 14-membered nonaromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8 membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2c]pyridinyl, 4,5,6,7-tetrahydrothieno[3,2-b]pyridinyl, 1,2,3,4 tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system.

"Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1,2,3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1,2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7 membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R—, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$))$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^f$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)+X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{99}$ substituents can be joined to form =O or =S; wherein X is a counterion.

In certain embodiments, the carbon atom substituents are independently halogen, substituted or unsubstituted $C_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R—, or —NR$^{bb}$C(=O)N(R$^{bb}$)$_2$. In certain embodiments, the carbon atom substituents are independently halogen, substituted or unsubstituted $C_{1-6}$ alkyl, —OR$^{aa}$, —SR—, —N(R$^{bb}$)$_2$, —CN, —SCN, or —NO$_2$.

The term "halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{aa}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_2$-10 alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4- methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^b$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{aa}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{aa})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

DETAILED DESCRIPTION OF THE INVENTION

DNA methylation patterns tend to be maintained in differentiated cells; however, the methylation of DNA exists as a dynamic process, reversible by the Ten-eleven translocation methylcytosine dioxygenase (TET) family of dioxygenases, coded by three separate genes (Tet1, Tet2, and Tet3). These isoenzymes recognize and oxidize 5-methylcytosine (5mC) to 5-hydroxymethylcytosine (5hmC), 5-formylcytosine (5fC), and 5-carboxylcytosine (5caC) via an Fe(II)/alphaketoglutarate-dependent mechanism. These oxidized cytosine derivatives, themselves persistent epigenetic marks can then function as intermediates subject to deamination and glycosylase-dependent excision and repair, leading to the reversal back to unmodified cytosine. The result is a cyclical epigenetic mechanism (Scheme 1).

Scheme 1.
Active DNA methylation and demethylation. DNA methylation is dynamically regulated by methyl writing enzymes (DNMTs) and methyl erasing enzymes (TETs), allowing the mechanism to govern local gene expression, a process important for cell function and identity.

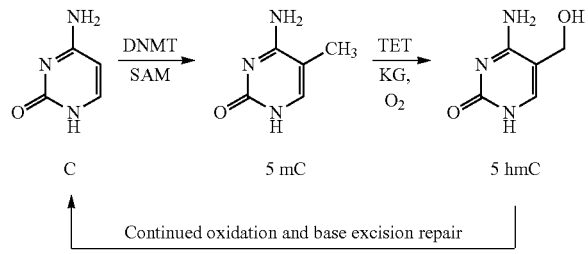

Disruption of DNA methylation patterns is known to be a hallmark of cancer with Tet2 being one of the most frequently mutated genes in hematopoietic malignancies. Likewise, mutations in Tet1, Tet2, and Tet3, eliciting reduced expression, impaired enzymatic activity, and concomitant decrease in levels of 5hmC, appear to impart a diverse range of mutational landscapes in a wide variety of different cancer types including liver, lung, gastric, prostate, and breast cancer as well as melanoma and glioblastoma.

Accordingly, the present disclosure provides cytosine analogs (e.g., a cytosine-based TET enzyme inhibitor), compositions comprising such analogs, and methods of using such analogs for inhibiting TET enzyme in a reaction and/or in a cell and/or in a subject in need thereof.

Cytosine Analogs

Aspects of the present disclosure provide a cytosine analog of Formula I

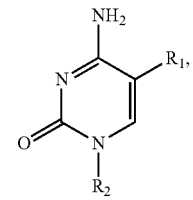

or a pharmaceutically acceptable salt thereof, wherein $R_1$ is independently selected from the group consisting of hydrogen, halogen, optionally substituted alkyl, optionally substituted alkenyl, or optionally substituted alkynyl, and wherein $R_2$ is selected from selected from the group consisting of hydrogen, optionally substituted carbocyclyl, optionally substituted heterocyclyl, optionally substituted aryl, or optionally substituted heteroaryl.

In some embodiments of any one of the compositions or methods provided herein, $R_1$ is hydrogen. In some embodiments of any one of the compositions or methods provided herein, $R_1$ is halogen. In some embodiments of any one of the compositions or methods provided herein, $R_1$ is fluorine. In some embodiments of any one of the compositions or methods provided herein, $R_1$ is chlorine. In some embodiments of any one of the compositions or methods provided herein, $R_1$ is bromine. In some embodiments of any one of the compositions or methods provided herein, $R_1$ is iodine.

In some embodiments of any one of the compositions or methods provided herein, $R_1$ is substituted alkyl. In some embodiments of any one of the compositions or methods provided herein, $R_1$ is unsubstituted alkyl. In some embodiments of any one of the compositions or methods provided herein, $R_1$ is substituted $C_{1-6}$ alkyl. In some embodiments of any one of the compositions or methods provided herein, $R_1$ is unsubstituted $C_{1-6}$ alkyl. In some embodiments of any one of the compositions or methods provided herein, $R_1$ is methyl. In some embodiments of any one of the compositions or methods provided herein, $R_1$ is fluoromethyl. In some embodiments of any one of the compositions or methods provided herein, $R_1$ is difluoromethyl. In some embodiments of any one of the compositions or methods provided herein, $R_1$ is trifluoromethyl.

In some embodiments of any one of the compositions or methods provided herein, $R_1$ is substituted alkenyl. In some embodiments of any one of the compositions or methods provided herein, $R_1$ is unsubstituted alkenyl. In some embodiments of any one of the compositions or methods provided herein, $R_1$ is vinyl. In some embodiments of any one of the compositions or methods provided herein, $R_1$ is ethenyl. In some embodiments of any one of the compositions or methods provided herein, $R_1$ is substituted alkynyl. In some embodiments of any one of the compositions or methods provided herein, $R_1$ is unsubstituted alkynyl. In some embodiments of any one of the compositions or methods provided herein, $R_1$ is ethynyl. In some embodiments of any one of the compositions or methods provided herein, $R_1$ is propargyl.

In some embodiments of any one of the compositions or methods provided herein, $R_2$ is hydrogen. In some embodiments of any one of the compositions or methods provided herein, $R_2$ is substituted carbocyclyl. In some embodiments of any one of the compositions or methods provided herein, $R_2$ is unsubstituted carbocyclyl. In some embodiments of any one of the compositions or methods provided herein, $R_2$ is substituted heterocyclyl. In some embodiments of any one of the compositions or methods provided herein, $R_2$ is unsubstituted heterocyclyl. In some embodiments of any one of the compositions or methods provided herein, $R_2$ is substituted aryl. In some embodiments of any one of the compositions or methods provided herein, $R_2$ is unsubstituted aryl. In some embodiments of any one of the compositions or methods provided herein, $R_2$ is substituted heteroaryl. In some embodiments of any one of the compositions or methods provided herein, $R_2$ is unsubstituted heteroaryl.

In some embodiments of any one of the compositions or methods provided herein, $R_2$ is of formula $-(CH_2)_nC(=O)N(R^A)_2$, wherein n is 1, 2, or 3; and each instance of $R^A$ is independently hydrogen, optionally substituted $C_{1-6}$ alkyl, or optionally substituted aryl. In some embodiments of any one of the compositions or methods provided herein, n is 1. In some embodiments of any one of the compositions or methods provided herein, n is 2. In some embodiments of any one of the compositions or methods provided herein, n is 3. In some embodiments of any one of the compositions or methods provided herein, $R^A$ is hydrogen. In some embodiments of any one of the compositions or methods provided herein, $R^A$ is substituted $C_{1-6}$ alkyl. In some embodiments of any one of the compositions or methods provided herein, $R^A$ is unsubstituted $C_{1-6}$ alkyl. In some embodiments of any one of the compositions or methods provided herein, $R^A$ is substituted aryl. In some embodiments of any one of the compositions or methods provided herein, $R^A$ is unsubstituted aryl.

In some embodiments of any one of the compositions or methods provided herein, $R_2$ is substituted phenyl. In some embodiments of any one of the compositions or methods provided herein, $R_2$ is unsubstituted phenyl. In some embodiments of any one of the compositions or methods provided herein, $R_2$ is phenyl substituted with halogen. In some embodiments of any one of the compositions or methods provided herein, $R_2$ is phenyl substituted with chlorine. In some embodiments of any one of the compositions or methods provided herein, $R_2$ is 4-chlorophenyl. In some embodiments of any one of the compositions or methods provided herein, $R_2$ is 3-chlorophenyl. In some embodiments of any one of the compositions or methods provided herein, $R_2$ is 2-chlorophenyl.

In some embodiments of any one of the compositions or methods provided herein, $R_2$ is phenyl substituted with $C_{1-6}$ alkyl. In some embodiments of any one of the compositions or methods provided herein, $R_2$ is 4-methylphenyl. In some embodiments of any one of the compositions or methods provided herein, $R_2$ is 3-methylphenyl. In some embodiments of any one of the compositions or methods provided herein, $R_2$ is 2-methylphenyl. In some embodiments of any one of the compositions or methods provided herein, $R_2$ is 2-biphenyl. In some embodiments of any one of the compositions or methods provided herein, $R_2$ is 3-biphenyl. In some embodiments of any one of the compositions or methods provided herein, $R_2$ is 4-biphenyl.

In some embodiments of any one of the compositions or methods provided herein, $R_2$ is substituted napthyl. In some embodiments of any one of the compositions or methods provided herein, $R_2$ is unsubstituted napthyl. In some embodiments of any one of the compositions or methods provided herein, $R_2$ is 1-napthyl. In some embodiments of any one of the compositions or methods provided herein, $R_2$ is 2-napthyl.

In some embodiments of any one of the compositions or methods provided herein $R_2$ is substituted heteroaryl. In some embodiments of any one of the compositions or methods provided herein, $R_2$ is unsubstituted heteroaryl. In some embodiments of any one of the compositions or methods provided herein, $R_2$ is substituted pyridyl. In some embodiments of any one of the compositions or methods provided herein, $R_2$ is unsubstituted pyridyl. In some embodiments of any one of the compositions or methods provided herein, $R_2$ is substituted quinolyl. In some embodiments of any one of the compositions or methods provided herein, $R_2$ is unsubstituted quinolyl. In some embodiments of any one of the compositions or methods provided herein, $R_2$ is substituted dibenzofuranyl. In some embodiments of any one of the compositions or methods provided herein, $R_2$ is unsubstituted dibenzofuranyl. In some embodiments of any one of the compositions or methods provided herein $R_2$ is substituted benzo[d]oxazolyl. In some embodiments of any one of the compositions or methods provided herein, $R_2$ is unsubstituted benzo[d]oxazolyl.

In some embodiments of any one of the compositions or methods provided herein, $R_2$ is nicotinonitrile. In some embodiments of any one of the compositions or methods provided herein, $R_2$ is 5-methoxypyridin-2-yl. In some embodiments of any one of the compositions or methods provided herein, $R_2$ is 4-dibenzofuranyl. In some embodiments of any one of the compositions or methods provided herein, $R_2$ is unsubstituted 3-quinolinyl. In some embodiments of any one of the compositions or methods provided herein, $R_2$ is 2-phenylbenzo[d]oxazol-6-yl. In some embodiments of any one of the compositions or methods provided herein, $R_2$ is 2-phenylbenzo[d]oxazol-7-yl.

In some embodiments of any one of the compositions or methods provided herein, $R_2$ is

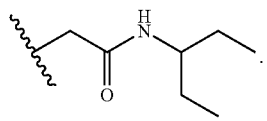 [SMILES: *CC(=O)NC(CC)CC]

In some embodiments of any one of the compositions or methods provided herein, $R_2$ is

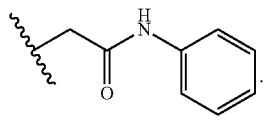 [SMILES: *CC(=O)Nc1ccccc1]

In some embodiments of any one of the compositions or methods provided herein, $R_2$ is

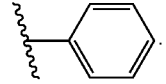

In some embodiments of any one of the compositions or methods provided herein, $R_2$ is

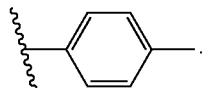

In some embodiments of any one of the compositions or methods provided herein, $R_2$ is

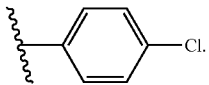

In some embodiments of any one of the compositions or methods provided herein, $R_2$ is

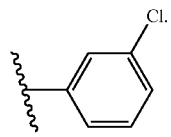 [SMILES: *c1cccc(Cl)c1]

In some embodiments of any one of the compositions or methods provided herein, $R_2$ is

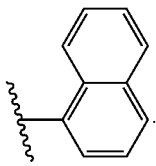 [SMILES: *c1cccc2ccccc12]

In some embodiments of any one of the compositions or methods provided herein, $R_2$ is

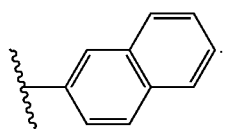 [SMILES: *c1ccc2ccccc2c1]

In some embodiments of any one of the compositions or methods provided herein, $R_2$ is

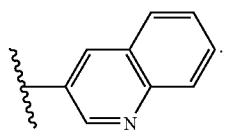

In some embodiments of any one of the compositions or methods provided herein, $R_2$ is

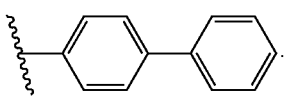

In some embodiments of any one of the compositions or methods provided herein, $R_2$ is

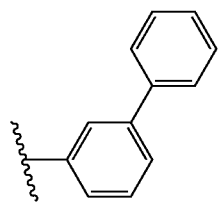

In some embodiments of any one of the compositions or methods provided herein, $R_2$ is

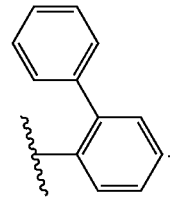 [SMILES: *c1ccccc1-c1ccccc1]

In some embodiments of any one of the compositions or methods provided herein, $R_2$ is

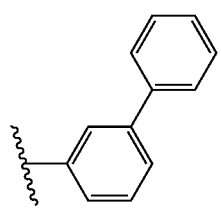

In some embodiments of any one of the compositions or methods provided herein, $R_2$ is

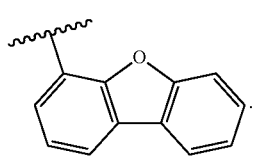 [SMILES: *c1cccc2c1oc1ccccc12]

In some embodiments of any one of the compositions or methods provided herein, $R_2$ is

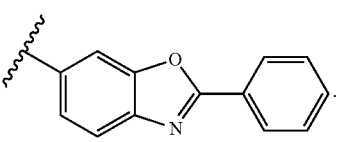 [SMILES: *c1ccc2nc(-c3ccccc3)oc2c1]

In some embodiments of any one of the compositions or methods provided herein, $R_2$ is

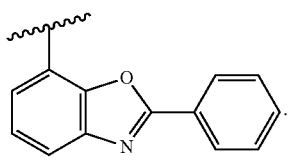 [SMILES: *c1cccc2nc(-c3ccccc3)oc12]

In some embodiments of any one of the compositions or methods provided herein, the cytosine analog is any one of the cytosine analogs provided herein. In some embodiments of any one of the compositions or methods provided herein, the cytosine analog of Formula I is the final product compound depicted in Example 2. In some embodiments of any one of the compositions or methods provided herein, the cytosine analog of Formula I is the final product compound depicted in Example 4. In some embodiments of any one of the compositions or methods provided herein, the cytosine analog of Formula I is the final product compound depicted in Example 4. In some embodiments of any one of the compositions or methods provided herein, the cytosine analog of Formula I is the final product compound depicted in Example 5. In some embodiments of any one of the compositions or methods provided herein, the cytosine analog of Formula I is the final product compound depicted in Example 6. In some embodiments of any one of the compositions or methods provided herein, the cytosine analog of Formula I is the final product compound depicted in Example 7. In some embodiments of any one of the compositions or methods provided herein, the cytosine analog of Formula I is the final product compound depicted in Example 8. In some embodiments of any one of the compositions or methods provided herein, the cytosine analog of Formula I is the final product compound depicted in Example 9. In some embodiments of any one of the compositions or methods provided herein, the cytosine analog of Formula I is the final product compound depicted in Example 10. In some embodiments of any one of the compositions or methods provided herein, the cytosine analog of Formula I is the final product compound depicted in Example 11. In some embodiments of any one of the compositions or methods provided herein, the cytosine analog of Formula I is the final product compound depicted in Example 12. In some embodiments of any one of the compositions or methods provided herein, the cytosine analog of Formula I is the final product compound depicted in Example 13. In some embodiments of any one of the compositions or methods provided herein, the cytosine analog of Formula I is the final product compound depicted in Example 14. In some embodiments of any one of the compositions or methods provided herein, the cytosine analog of Formula I is the final product compound depicted in Example 15. In some embodiments of any one of the compositions or methods provided herein, the cytosine analog of Formula I is the final product compound depicted in Example 16. In some embodiments of any one of the compositions or methods provided herein, the cytosine analog of Formula I is the final product compound depicted in Example 17.

Cytosine analogs provided herein may bind any TET enzyme. In some embodiments of any one of the compositions or methods provided herein, the cytosine analog binds to a TET enzyme selected from the group consisting of TET1, TET2, and TET3. In some embodiments of any one of the compositions or methods provided herein, the cytosine analog binds to TET1, TET2, and TET3. In some embodiments of any one of the compositions or methods provided herein, the cytosine analog binds to TET1 and TET2. In some embodiments of any one of the compositions or methods provided herein, the cytosine analog binds to TET2 and TET3. In some embodiments of any one of the compositions or methods provided herein, the cytosine analog binds to TET1 and TET3. In some embodiments of any one of the compositions or methods provided herein, the cytosine analog binds to TET1. In some embodiments of any one of the compositions or methods provided herein, the cytosine analog binds to TET2. In some embodiments of any one of the compositions or methods provided herein, the cytosine analog binds to TET3.

In some embodiments of any one of the compositions or methods provided herein, the cytosine analog selectively binds to a TET enzyme as compared to another TET enzyme (e.g., selectively binds to TET1 as compared to TET2). A cytosine analog is said to "selectively bind" if it reacts or associates more frequently, more rapidly, with greater duration and/or with greater affinity for with a particular TET enzyme than it does with an another TET enzyme. For example, a cytosine analog selectively binds to TET1 if it binds with greater affinity, avidity, more readily, and/or with greater duration than it binds to another TET enzyme (e.g., TET 2). It is also understood that a cytosine analog that selectively binds TET1 may or may not specifically or preferentially bind to another TET enzyme (e.g., TET2). As such, "selectively binds" or preferentially binds does not necessarily require (although it can include) exclusive binding. In some embodiments of any one of the compositions or methods provided herein, the cytosine analog exclusively binds a TET enzyme (and does not bind another enzyme including another TET enzyme above background or what would be considered non-specific binding).

In some embodiments of any one of the compositions or methods provided herein, the cytosine analog selectively binds TET1 over TET2 and/or TET3. In some embodiments of any one of the compositions or methods provided herein, the cytosine analog selectively binds TET2 over TET1 and/or TET3. In some embodiments of any one of the compositions or methods provided herein, the cytosine analog selectively binds TET3 over TET1 and/or TET2.

In some embodiments of any one of the compositions or methods provided herein, the selectivity is between about 2-fold and about 5-fold. In some embodiments of any one of the compositions or methods provided herein, the selectivity is between about 5-fold and about 10-fold. In some embodiments of any one of the compositions or methods provided herein, the selectivity is between about 10-fold and about 20-fold. In some embodiments of any one of the compositions or methods provided herein, the selectivity is between about 20-fold and about 50-fold. In some embodiments of any one of the compositions or methods provided herein, the selectivity is between about 50-fold and about 100-fold. In some embodiments of any one of the compositions or methods provided herein, the selectivity is between about 100-fold and about 200-fold. In some embodiments of any one of the compositions or methods provided herein, the selectivity is between about 200-fold and about 500-fold. In some embodiments of any one of the compositions or methods provided herein, the selectivity is between about 500-fold and about 1000-fold. In some embodiments of any one of the compositions or methods provided herein, the selectivity is at least about 1000-fold.

In some embodiments of any one of the compositions or methods provided herein, the cytosine analog inhibits an activity of a TET enzyme (e.g., oxidation of 5mC to 5hmC)

by at least 10%, at least 20%, at least 30%, at least 40%, at least 50%, at least 60%, at least 70%, at least 80%, at least 90%, at least 99%, or at least 100%. In some embodiments of any one of the compositions or methods provided herein, the cytosine analog inhibits an activity of TET1 (e.g., oxidation of 5mC to 5hmC) by at least 10%, at least 20%, at least 30%, at least 40%, at least 50%, at least 60%, at least 70%, at least 80%, at least 90%, at least 99%, or at least 100%. In some embodiments of any one of the compositions or methods provided herein, the cytosine analog inhibits an activity of TET2 (e.g., oxidation of 5mC to 5hmC) by at least 10%, at least 20%, at least 30%, at least 40%, at least 50%, at least 60%, at least 70%, at least 80%, at least 90%, at least 99%, or at least 100%. In some embodiments of any one of the compositions or methods provided herein, the cytosine analog inhibits an activity of TET3 (e.g., oxidation of 5mC to 5hmC) by at least 10%, at least 20%, at least 30%, at least 40%, at least 50%, at least 60%, at least 70%, at least 80%, at least 90%, at least 99%, or at least 100%.

Cytosine Analog-Containing Compositions

In some embodiments, one or more cytosine analogs described herein can be mixed with a pharmaceutically acceptable carrier (excipient) to form a pharmaceutical composition, which can be used for treating any one of the conditions, including diseases, as described herein. "Acceptable" means that the carrier must be compatible with the active ingredient of the composition (and preferably, in some embodiments, capable of stabilizing the active ingredient) and not deleterious to the subject to be treated. Pharmaceutically acceptable excipients (carriers), including buffers, are well known in the art. See, e.g., Remington: The Science and Practice of Pharmacy 20th Ed. (2000) Lippincott Williams and Wilkins, Ed. K. E. Hoover.

Pharmaceutically acceptable carriers include, but are not limited to, diluents, fillers, salts, buffers, stabilizers, solubilizers and other materials which are well-known in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The cytosine analog-containing pharmaceutical compositions as described herein can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are generally nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In other examples, the pharmaceutical composition described herein can be formulated in sustained-release format. Suitable examples of sustained-release preparations include semipermeable matrices of solid hydrophobic polymers containing cytosine analogs, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration are preferably sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, a cytosine analog can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

In some embodiments, any one of the cytosine analog-containing pharmaceutical compositions may further comprise an additional therapeutic agent based on the intended therapeutic uses of the composition. For example, a cytosine analog-containing pharmaceutical composition may comprise an additional therapeutic agent for treating a neurological disorder. Such therapeutic agents include, but are not limited to Donepezil, Tacrine, Rivastigmine, memantine (AXURA™, AKATINOL™, NAMENDA™, EBIXA™, ABIXA™), aricept, physostigmine, nicotine, arecoline, huperzine alpha, selegiline, Rilutek™ (riluzole), vitamin c, vitamin e, carotenoids, *Ginkgo biloba*, and the like.

Methods of Use

Any one of the cytosine analogs provided herein may be useful for non-clinical purposes (e.g., research purposes). For example, any one of the cytosine analogs provided herein may be used to study DNA methylation in cells, such as cancer cells, and/or mechanisms of DNA methylation in cells, such as cancer cells (e.g., for discovery of novel biological pathways or processes involved in DNA methylation (e.g., in cancer development and/or metastasis).

Accordingly, aspects of the present disclosure provide methods for inhibiting a TET enzyme, comprising contacting any one of the cytosine analogs provided herein with a TET enzyme, which may be any TET enzyme, such as any one of the TET enzymes provided herein.

In some embodiments of any one of the methods provided, the method comprises inhibiting a TET enzyme selected from the group consisting of TET 1, TET 2, and TET3. In some embodiments of any one of the methods provided, the method comprises inhibiting TET1. In some embodiments of any one of the methods provided, the method comprises inhibiting TET2. In some embodiments of any one of the methods provided, the method comprises inhibiting TET3.

Methods provided herein can comprise contacting any one of the cytosine analogs described herein with a TET enzyme under any conditions suitable for inhibiting the TET enzyme. In some embodiments of any one of the methods provided, contacting a cytosine analog and a TET enzyme comprises exposing the cytosine analog to the TET enzyme for a suitable period sufficient for inhibiting TET enzyme-mediated oxidation of methylated DNA. In some embodiments of any one of the methods provided, contacting occurs in vitro. In some embodiments of any one of the methods provided, contacting occurs in vivo. In some embodiments of any one of the methods provided, contacting occurs in a cell. In some embodiments of any one of the methods provided, contacting occurs in the cell of a subject.

Various concentrations of a cytosine analog may be contacted with a TET enzyme. In some embodiments, the concentration of a cytosine analog contacted with a TET enzyme is between 1 µM and 500 µM.

In some embodiments, the concentration of a cytosine analog contacted with a TET enzyme is between 10 µM and 500 µM, between 20 µM and 500 µM, between 30 µM and 500 µM, between 40 µM and 500 µM, between 50 µM and 500 µM, between 60 µM and 500 µM, between 70 µM and 500 µM, between 80 µM and 500 µM, between 90 µM and 500 µM, between 100 µM and 500 µM, between 200 µM and 500 µM, between 300 µM and 500 µM, or between 400 µM and 500 µM.

In some embodiments, the concentration of a cytosine analog contacted with a TET enzyme is between 1 µM and 400 µM, between 1 µM and 300 µM, between 1 µM and 200 µM, between 1 µM and 100 µM, between 1 µM and 90 µM, between 1 µM and 80 µM, between 1 µM and 70 µM, between 1 µM and 60 µM, between 1 µM and 50 µM, between 1 µM and 40 µM, between 1 µM and 30 µM, between 1 µM and 20 µM, or between 1 µM and 10 µM.

A cytosine analog may be contacted with a TET enzyme for any length of time. In some embodiments, a cytosine analog is contacted with a TET enzyme for at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, or at least 55 minutes. In some embodiments, a cytosine analog is contacted with a TET enzyme for at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 24 hours, at least 36 hours, or at least 48 hours.

Cytosine analogs provided herein may be useful for clinical purposes (e.g., patient treatment). For example, a method for inhibiting a TET enzyme in a subject comprises administering to the subject a therapeutically effective amount of any one of the cytosine analogs provided herein. In some embodiments of any one of the methods provided herein, the subject has or is at risk of having any one of the conditions provided herein.

As used herein, "a subject" refers to a mammal being assessed for treatment and/or being treated. Subjects may be human, but also include other mammals, particularly those mammals useful as laboratory models for human disease (e.g., mouse models).

As used herein, the term "treating" refers to administration of a composition comprising a cytosine analog provided herein to a subject, who is in need of the treatment, for example, having a condition (including a disease or disorder) provided herein, a symptom of the condition, or a predisposition toward the condition, with the purpose to cure, heal, alleviate, relieve, alter, remedy, ameliorate, improve, or affect the condition, one or more symptoms of the condition, or the predisposition toward the condition.

Alleviating a condition includes delaying the development or progression of the condition, or reducing the severity of the condition. Alleviating the condition does not necessarily require curative results. As used therein, "delaying" the development of a condition means to defer, hinder, slow, retard, stabilize, and/or postpone progression of the condition. This delay can be of varying lengths of time, depending on the history of the condition and/or individuals being treated. A method that "delays" or alleviates the development of a condition, or delays the onset of the condition, is a method that reduces probability of developing one or more symptoms of the condition in a given time frame and/or reduces extent of the symptoms in a given time frame, when compared to not using the method. Such comparisons are typically based on clinical studies, using a number of subjects sufficient to give a statistically significant result.

"Development" or "progression" of a condition means initial manifestations and/or ensuing progression of the condition. Development of the condition can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a condition includes initial onset and/or recurrence.

A human subject who needs the treatment may be a human patient having, at risk for, or suspected of having a condition, such as dysregulated DNA methylation. Examples of conditions associated with dysregulated DNA methylation include, but are not limited to, cancers, autoimmune diseases, metabolic disorders, and neurological disorders.

Any one of the methods and compositions described herein may be used to treat a cancer. Examples of cancer include, but are not limited to, liver cancer, lung cancer, gastric cancer, prostate cancer, breast cancer, hematological cancer, melanoma, and glioblastoma or any one of the other cancers described herein.

Any one of the methods and compositions described herein may be used to treat a neurological disorder. Examples of such disorders include cognitive disorders. "Cognitive disorder" refers to a disorder where there is a reduction or impairment of one or more cognitive abilities including learning, memory, perception, and problem solving. Cognitive disorders include, but are not limited to, mild neurocognitive disorder, dementia, Alzheimer's disease, Parkinson's disease, and schizophrenia. Cognitive disorders also include intellectual disabilities. Examples of intellectual disabilities include, but are not limited to, nucleotide repeat disorder, fragile X syndrome, Angelman syndrome, Prader-Willi syndrome, Rett syndrome, ATR-X syndrome, Rubenstein-Taybi syndrome, and Kleefstra syndrome.

A subject having a condition can be identified by routine medical examination, e.g., laboratory tests, organ functional tests, and/or behavior tests. A subject suspected of having any one of such conditions might show one or more symptoms of the condition. A subject at risk for the condition can be a subject having one or more of the risk factors for that condition, for example, a genetic factor.

As used herein, "an effective amount" refers to the amount of cytosine analog described herein required to confer a therapeutic effect, either alone or in combination with one or more additional therapeutic agents, such as one or more additional therapeutic agents for treating a condition. In some embodiments of any one of the methods or compositions provided herein, the therapeutic effect is to inhibit the activity of a TET enzyme (e.g., by at least 10%, 20%, 30%, 40%, 50%, 60%, 70%, 80%, 90%, 95%, or higher) in the subject. In some embodiments of any one of the methods or compositions provided herein, the therapeutic effect is to alter DNA methylation (e.g., by at least 10%, 20%, 30%, 40%, 50%, 60%, 70%, 80%, 90%, 95%, or higher) in the subject. In some embodiments of any one of the methods or compositions provided herein, the therapeutic effect is improvement of basic behavioral functioning, and/or improvement of cognitive functioning. In some embodiments of any one of the methods or compositions provided herein, the therapeutic effect is alleviating one or more symptoms associated with any one of the conditions provided herein.

Determination of whether an amount of the composition as described herein achieves the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target condition. Alternatively, sustained continuous release formulations of a composition as described herein may be appropriate. Various formulations and devices for achieving sustained release are known in the art.

Generally, for administration of any one of the compositions, an exemplary daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a condition, or a symptom thereof. An exemplary dosing regimen comprises administering one or more initial doses at an suitable interval over a suitable period. If necessary, multiple maintenance doses can be given to the subject at a suitable interval over a suitable period of time. However, other dosage regimens may be useful, depending on the pattern of pharmacokinetic decay that the practitioner wishes to achieve. For example, dosing from one to four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency can be twice a day, once a day, once every other day, once every week, once every 2 weeks, or once every 4 weeks. The dosing regimen can vary over time.

In some embodiments, for an adult patient of normal weight, doses ranging from about 0.3 to 5.0 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a cytosine analog as described herein will depend on the specific cytosine analog, and/or other active ingredient employed, the type and severity of the condition, whether the composition is administered for preventive or therapeutic purposes, previous therapy, the patient's clinical history and response to the cytosine analog, and the discretion of the attending physician. Typically the clinician will administer a composition, until a dosage is reached that achieves the desired result.

Conventional methods, known to those of ordinary skill in the art of medicine, can be used to administer the composition (e.g., a pharmaceutical composition) to the subject, depending upon the type of condition to be treated or the site of the condition. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, a pharmaceutical formulation containing a cytosine analog provided herein and a physiologically acceptable excipient can be infused. Physiologically acceptable excipients may include, for example, 5% dextrose, 0.9% saline, Ringer's solution or other suitable excipients. Intramuscular preparations, e.g., a sterile formulation of a suitable soluble salt form of a cytosine analog provided herein, can be dissolved and administered in a pharmaceutical excipient such as Water-for-Injection, 0.9% saline, or 5% glucose solution.

In some embodiments, a cytosine analog-containing composition is administered via a site-specific or targeted local delivery technique. Examples of site-specific or targeted local delivery techniques include various implantable depot sources of the cytosine analog-containing composition or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Treatment efficacy for a condition can be assessed by methods well-known in the art.

EXAMPLES

In order that the invention described herein may be more fully understood, the following examples are set forth. The examples described in this application are offered to illustrate the methods and compositions provided herein and are not to be construed in any way as limiting their scope.

Example 1: Cytosine Analog Synthesis and Characterization

Cytosine analogs were prepared by a two-step synthesis as shown in Scheme 2. First, the 5 position of cytosine was halogenated (or alkylated) by taking advantage of the preference for cytosine to undergo electrophilic aromatic substitution at this position. For example, 5-chlorosytosine was synthesized using N-chlorosuccinimide (NCS) in refluxing acetic acid. Second, the N1 position of the cytosine derivative was coupled using copper-mediated Ullman conditions to phenylboronic acid.

Scheme 2.
Cytosine-based TET enzyme inhibitor two-step synthesis. First step comprises electrophilic aromatic substitution with cytosine and N-chlorosuccinimide. Second step comprises copper catalyzed boronic acid coupling with 5-chlorocytosine and phenylboronic acid to yield wanted product.

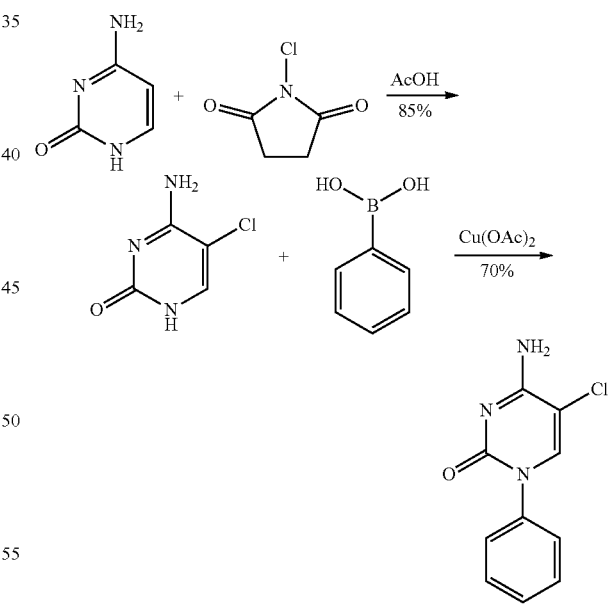

General Synthetic Materials and Methods.

All nonaqueous reactions were conducted in oven and flame-dried glassware under nitrogen atmosphere with dry solvents and magnetic stirring. The nitrogen was dried by passing through a tube of Drierite. Dichloromethane (CH2Cl2 or DCM), methanol (MeOH), anhydrous tetrahydrofuran (THF), ethyl acetate (EtOAc), and dimethyl sulfoxide (DMSO) were purchased from Aldrich Chemicals or Fisher Scientific and used as received. All other reagents were purchased from Acros Chemicals, Aldrich Chemicals, and Bachem. Reactions were monitored by thin layer chromatography (TLC) using 0.25 mm Whatman precoated silica gel plates. Column chromatography was performed with the indicated solvents and Dynamic Absorbents silica gel (particle size 0.023-0.040 mm). Proton (1H) and carbon (13C) NMR spectra were 54 recorded on Bruker Avance 400 at 300 K. Chemical shifts are reported in ppm (δ) values relative to DMSO-d6 (δ 2.50 for proton and δ 39.5 for carbon NMR). TLC plates were stained with Seebach's Dip 25 mL concentrated sulfuric acid was added dropwise to a solution of 25 g phosphomolybdic acid and 7.5 g cerium (IV) sulfate in 479 mL water.

General Procedure A: Cytosine and Boronic Acid Coupling.

Boronic acid (1.5 eq.) and Cu(OAC)$_2$ (1.0 eq.) were added while stirring to a 0.5 M solution of cytosine/chlorocytosine (1.0 eq.) in a 3:1 mixture (by volume) of MeOH:H2O. Then, TMEDA (2.0 eq.) was added dropwise. The reaction was stirred for 4 h at room temperature and monitored by TLC. Then, the reaction was evaporated to dryness and purified by column chromatography.

Liquid Chromatography and Mass Spectrometry for Evaluation of Chemical Purity.

Compounds submitted for biological evaluation were determined to be >95% pure by LCMS evaluation performed by the Mass Spectrometry Laboratory in the School of Chemical Sciences at the University of Illinois Urbana-Champagne (Urbana, Ill.). High performance liquid chromatography mass spectrometry (LCMS) was carried out using an Agilent 2.1×50 mm C-18 column and a Micromass Q-tof Ultima mass spectrometer. Mobile phase A consisted of HPLC grade H2O with 0.01% Formic Acid; mobile phase B consisted of MeCN with 0.01% Formic Acid. LCMS identification and purity utilized a binary gradient starting with 90% A and 10% B and linearly increasing to 100% B over the course of 6 min, followed by an isocratic flow of 100% B for an additional 3 min. A flow rate of 0.5 mL/min was maintained throughout the HPLC method. The purity of all products was determined by integration of the total ion count (TIC) spectra and integration of the ultraviolet (UV) spectra at 214 nm. Retention times are abbreviated tR; mass to charge ratios are abbreviated as m/z.

Example 2: Synthesis and Characterization of 5-chloro-cytosine

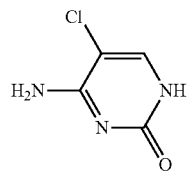

To a 0.6 M solution of Cytosine (1.0 eq.) in glacial acetic acid was added N-chlorosuccinimide (1.1 eq.) and heated for 4 hours at 70° C. Acetic acid was evaporated under low pressure. The crude solid was diluted with 60 mL of distilled water and sodium bicarbonate slowly added until the solution was pH 9. The solid was then filtered under vacuum. 84.4%. White solid. $^1$H NMR (400 MHz, DMSO) δ 11.00 (brs, 1H), 7.85 (s, 1H), 7.20 (brs, 2H). $^{13}$C NMR (400 MHz, DMSO) δ 162.22, 156.94, 143.63, 97.99.

Example 3: Synthesis and Characterization of 5-bromo-cytosine

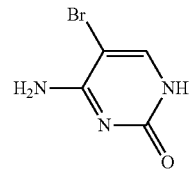

To a 0.6 M solution of Cytosine (1.0 eq.) in glacial acetic acid was added N-bromosuccinimide (1.1 eq.) and heated for 4 hours at 70° C. Acetic acid was evaporated under low pressure. The crude solid was diluted with 60 mL of distilled water and sodium bicarbonate slowly added until the solution was pH 9. The solid was then filtered under vacuum. 65.5%. White solid. $^1$H NMR (400 MHz, DMSO) δ 11.00 (brs, 1H), 7.75 (s, 1H), 7.10 (brs, 2H). $^{13}$C NMR (400 MHz, DMSO) δ 162.67, 156.66, 145.47, 85.17.

Example 4: Synthesis and Characterization of 5-trifluoromethyl-cytosine

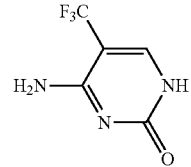

To a 0.4 M solution of cytosine (1.0 eq.) in DMSO was added iron (II) sulfate (1.0 eq.), hydrogen peroxide (0.26 eq.), sulfuric acid (0.01 eq.), and trifluoromethyl iodide in excess (via balloon). The reaction was then stirred at r.t. for 2 hours, then the pH of the reaction was to 8-9 using saturated sodium bicarbonate. The reaction was then filtered and the eluent purified by column chromatography (4:1 DCM to MeOH). 36%. White solid. $^1$H NMR (400 MHz, DMSO) δ 7.95 (s, 1H), 7.85 (brs, 1H), 6.95 (brs, 2H). $^{13}$C NMR (400 MHz, DMSO) δ 161.5, 156, 145, 124, 94.3 (q, CF3).

Example 5: Synthesis and Characterization of 4-amino-5-chloro-1-phenylpyrimidin-2(1H)-one-(Bobcat216)

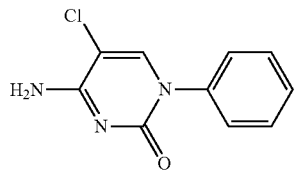

General procedure A was used to couple chlorocytosine (250 mg, 1.72 mmol) and phenylboronic acid (1.5 eq.) to yield title compound. 70%. White powder. R$_f$=0.55 (8.3% MeOH in DCM; Seebach's Dip). $^1$H NMR (400 MHz, DMSO) δ 11.95 (s, 1H), 8.07 (s, 1H), 7.43 (m, 5H), 7.31 (s, 1H). $^{13}$C NMR (100 MHz, DMSO) δ 162.40, 153.88, 144.18, 141.01, 129.81, 129.25, 128.19, 127.17. LCMS: $t_R$=3.13; m/z=380.3. HRMS m/z calc. for $C_{10}H_8N_3OCl$ (M+H), 222.0434; found, 222.0432.

Example 6: Synthesis and Characterization of 4-amino-5-bromo-1-phenylpyrimidin-2(1H)-one-(Bobcat371)

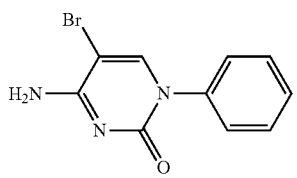

General Procedure A was used to couple bromocytosine (380 mg, 2.0 mmol) and phenylboronic acid (1.5 eq.) to yield title compound. 74%. $R_f$=0.60 (10% MeOH in DCM; Seebach's Dip). $^1$H NMR (400 MHz, DMSO) δ 8.10 (s, 1H), 8.05-7.87 (brs, 1H), 7.50-7.35 (m, 5H), 7.15-7.07 (brs, 1H). $^{13}$C NMR (100 MHz, DMSO) δ 162.89, 154.10, 146.74, 140.77, 129.26, 128.21, 127.16, 86.98. LCMS: $t_R$=3.31; m/z=266.0. HRMS m/z calc. for $C_{10}H_8N_3OBr$ (M+H), 265.9929; found, 265.9929.

Example 7: Synthesis and Characterization of 4-amino-1-phenyl-5-(trifluoromethyl)pyrimidin-2(1H)-one (Bobcat212)

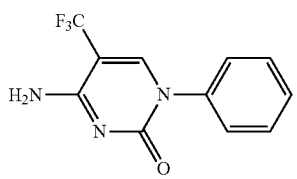 [SMILES: Nc1nc(=O)n(-c2ccccc2)cc1Cl]

General procedure A was used to couple trifluorocytosine (43 mg, 0.24 mmol) and phenylboronic acid (1.5 eq.) to yield title compound. 25%. White powder. $R_f$=0.65 (8.3% MeOH in DCM; UV active). $^1$H NMR (400 MHz, DMSO) δ 8.23 (d, 1H), 8.01 (s, 1H), 7.45 (m, 5H), 7.16 (s, 1H). 13C NMR (100 MHz, DMSO) δ 172.49, 161.03, 154.00, 148.21, 140.53, 129.30, 128.59, 127.35, 95.33 (q, CF$_3$). LCMS: $t_R$=3.85; m/z=256.1. HRMS m/z calc. for $C_{11}H_8N_3OF_3$ (M+H), 256.0598; found, 256.0694.

Example 8: Synthesis and Characterization of 4-amino-5-chloro-1-(p-tolyl)pyrimidin-2(1H)-one-(Bobcat308)

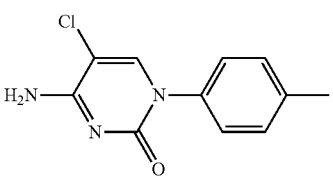 [SMILES: Cc1ccc(-n2cc(Cl)c(N)nc2=O)cc1]

General procedure A was used to couple chlorocytosine (250 mg, 1.72 mmol) and p-tolylboronic acid (1.5 eq.) to yield title compound. 78%. White powder. $R_f$=0.55 (10% MeOH in DCM; Seebach's Dip). $^1$H NMR (400 MHz, DMSO) δ 8.25 (m, 1H), 7.42 (m, 5H), 5.83 (m, 1H), 2.18 (s, 3H). $^{13}$C NMR (100 MHz, DMSO) δ 162.42, 154.15, 144.19, 138.37, 137.66, 129.68, 126.85, 55.38, 21.08. LCMS: $t_R$=3.90; m/z=236.1. HRMS m/z calc. for $C_{11}H_{10}N_3OCl$ (M+H), 236.0591; found, 236.0589.

Example 9: Synthesis and Characterization of 4-amino-5-chloro-1-(4-chlorophenyl)pyrimidin-2(1H)-one (Bobcat218)

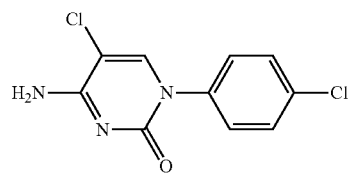 [SMILES: Nc1nc(=O)n(-c2ccc(Cl)cc2)cc1Cl]

General procedure A was used to couple chlorocytosine (250 mg, 1.72 mmol) and 4-chloroboronic acid (1.5 eq.) to yield title compound. 47%. White powder. $R_f$=0.5 (10% MeOH in DCM; Seebach's Dip). $^1$H NMR (400 MHz, DMSO) δ 8.08 (s, 1H), 8.01 (s, 1H), 7.48 (m, 4H), 7.35 (s, 1H). $^{13}$C NMR (100 MHz, DMSO) δ 162.43, 153.82, 144.00, 139.58, 132.61, 129.56, 129.15, 129.09. LCMS: $t_R$=4.03; m/z=256.0. HRMS m/z calc. for $C_{10}H_7N_3OCl_2$ (M+H), 256.0044; found, 256.0040.

Example 10: Synthesis and Characterization of 4-amino-5-chloro-1-(3-chlorophenyl)pyrimidin-2(1H)-one (Bobcat205)

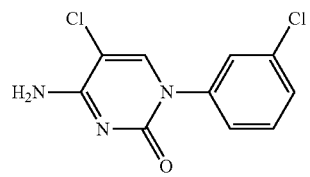

General procedure A was used to couple chlorocytosine (250 mg, 1.72 mmol) and 3-chlorophenylboronic acid (1.5 eq.) to yield title compound. 41%. White powder. $R_f$=0.8 (10% MeOH in DCM; Seebach's Dip). $^1$H NMR (400 MHz, DMSO) δ 8.13 (s, 2H), 7.55 (s, 1H), 7.42 (m, 4H). $^{13}$C NMR (100 MHz, DMSO) δ 162.54, 153.64, 143.95, 142.04, 133.28, 130.79, 128.19, 127.41, 126.07. LCMS: $t_R$=4.01; m/z=256.0. HRMS m/z calc. for $C_{10}H_7N_3OCl_2$ (M+H), 256.0044; found, 256.0041.

Example 11: Synthesis and Characterization of 4-amino-5-chloro-1-(naphthalen-1-yl)pyrimidin-2(1H)-one (Bobcat374)

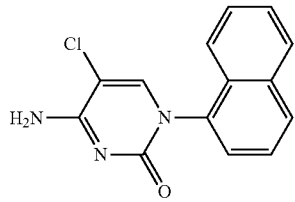 [SMILES: Nc1nc(=O)n(-c2cccc3ccccc23)cc1Cl]

General procedure A was used to couple chlorocytosine (291 mg, 2.0 mmol) and naphthalene-1-ylboronic acid (1.5 eq.) to yield title compound. 34%. $R_f$=0.5 (10% MeOH in DCM; Seebach's Dip). $^1$H NMR (400 MHz, DMSO) δ 8.00-7.95 (m, 2H), 7.70-7.63 (m, 1H), 7.61-7.52 (m, 4H), 7.48 (dd, J=7.3, 1H), 7.28 (s, 1H), 5.92-5.77 (brs, 1H). $^{13}$C NMR (100 MHz, DMSO) δ 162.80, 154.49, 145.11, 137.57, 134.20, 130.02, 129.33, 128.70, 128.68, 127.63, 126.99, 126.16, 126.09, 122.97. LCMS: $t_R$=4.37; m/z=272.1. HRMS m/z calc. for $C_{14}H_{10}N_3OCl$(M+H), 272.0591; found, 272.0587.

Example 12: Synthesis and Characterization of 4-amino-5-chloro-1-(naphthalen-2-yl)pyrimidin-2(1H)-one (Bobcat330)

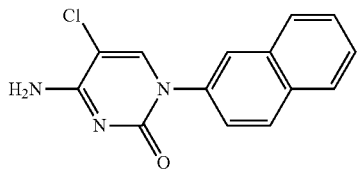

General procedure A was used to couple chlorocytosine (250 mg, 1.72 mmol) and naphthalene-2-ylboronic acid (1.5 eq.) to yield title compound. 54%. $R_f$=0.5 (10% MeOH in DCM; Seebach's Dip). $^1$H NMR (400 MHz, DMSO) δ 8.21 (s, 1H), 8.05 (s, 1H), 7.96 (m, 4H), 7.57 (m, 3H), 7.39 (s, 1H). $^{13}$C NMR (100 MHz, DMSO) δ 163.53, 154.16, 144.40, 138.57, 133.30, 132.42, 128.59, 128.38, 128.01, 127.10, 127.07, 125.80, 125.05. LCMS: $t_R$=4.58; m/z=272.1. HRMS m/z calc. for $C_{14}H_{10}N_3OCl$ (M+H), 272.0591; found, 272.0584.

Example 13: Synthesis and Characterization of 4-amino-5-chloro-1-(quinolin-3-yl)pyrimidin-2(1H)-one (Bobcat211)

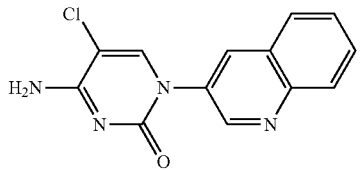 [SMILES: Nc1nc(=O)n(-c2cnc3ccccc3c2)cc1Cl]

General procedure A was used to couple chlorocytosine (113.5 mg, 0.78 mmol) and 3-quinoline boronic acid pinacol ester (1.5 eq.) to yield title compound. 41%. White powder. $R_f$=0.55 (8.3% MeOH in DCM; Seebach's Dip). $^1$H NMR (400 MHz, DMSO) δ 8.94 (d, 1H), 8.46 (d, 1H), 8.31 (s, 1H), 8.06 (m, 3H), 7.83 (ddd, 1H), 7.48 (s, 1H). $^{13}$C NMR (100 MHz, DMSO) δ 162.71, 154.13, 149.81, 146.53, 144.15, 134.38, 132.63, 130.49, 129.10, 128.68, 127.79, 127.72, 100.39. LCMS: $t_R$=3.45; m/z=273.1. HRMS m/z calc. for $C_{13}H_9N_4OCl$ (M+H), 273.0543; found, 273.0539.

Example 14: Synthesis and Characterization of 1-([1,1'-biphenyl]-4-yl)-4-amino-5-chloropyrimidin-2(1H)-one (Bobcat219)

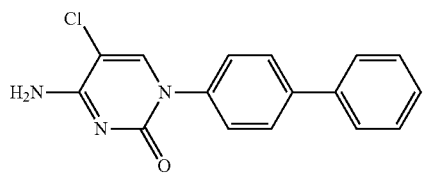 [SMILES: Nc1nc(=O)n(-c2ccc(-c3ccccc3)cc2)cc1Cl]

General procedure A was used to couple chlorocytosine (250 mg, 1.72 mmol) and 4-biphenylboronic acid (1.5 eq.) to yield title compound. 72%. White powder. $R_f$=0.65 (10% MeOH in DCM; Seebach's Dip). $^1$H NMR (400 MHz, DMSO) δ 8.13 (s, 1H), 7.94 (d, 1H), 7.72 (m, 4H), 7.49 (m, 4H), 7.41 (m, 1H), 7.35 (s, 1H). $^{13}$C NMR (100 MHz, DMSO) δ 162.40, 154.00, 144.18, 140.10, 139.99, 139.75, 129.49, 128.19, 127.64, 127.47, 127.22. LCMS: $t_R$=5.15; m/z=298.1. HRMS m/z calc. for $C_{16}H_{12}N_3OCl$ (M+H), 298.0747; found, 298.0746.

Example 15: Synthesis and Characterization of 1-([1,1'-biphenyl]-3-yl)-4-amino-5-chloropyrimidin-2(1H)-one (Bobcat339)

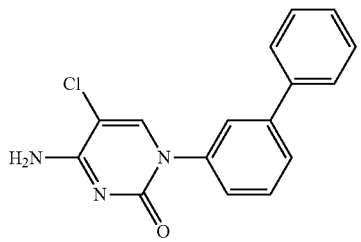 [SMILES: Nc1nc(=O)n(-c2cccc(-c3ccccc3)c2)cc1Cl]

General procedure A was used to couple chlorocytosine (250 mg, 1.72 mmol) and 2-biphenylboronic acid (1.5 eq.) to yield title compound. 79%. Green powder. $R_f$=0.50 (10% MeOH in DCM; Seebach's Dip). $^1$H NMR (400 MHz, DMSO) δ 8.20 (s, 1H), 8.03 (s, 1H), 7.70 (m, 4H), 7.44 (m, 6H). 13C NMR (100 MHz, DMSO) δ 162.50, 153.98, 144.33, 141.45, 141.38, 139.67, 129.74, 129.43, 128.80, 128.28, 127.28, 126.34, 126.22, 125.36. LCMS: $t_R$=5.09; m/z=298.1. HRMS m/z calc. for $C_{16}H_{12}N_3OCl$ (M+H), 298.0747; found, 298.0749.

Example 16: Synthesis and Characterization of 1-([1,1'-biphenyl]-2-yl)-4-amino-5-chloropyrimidin-2(1H)-one (Bobcat337)

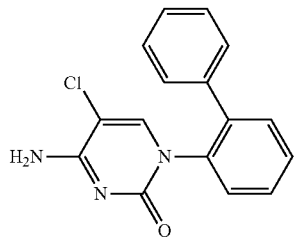 [SMILES: Nc1nc(=O)n(-c2ccccc2-c2ccccc2)cc1Cl]

General procedure A was used to couple chlorocytosine (250 mg, 1.72 mmol) and 2-biphenylboronic acid (1.5 eq.) to yield title compound. 9%. White powder. $R_f$=0.45 (10% MeOH in DCM; Seebach's Dip). $^1$H NMR (400 MHz, DMSO) δ 11.95 (s, 1H), 7.82 (s, 1H), 7.35 (m, 9H), 7.18 (s, 1H). $^{13}$C NMR (100 MHz, DMSO) δ 162.24, 154.55, 144.71, 139.68, 138.50, 138.44, 130.99, 129.44, 1.29.36, 128.92, 128.80, 127.96. LCMS: $t_R$=4.72; m/z=298.1. HRMS m/z calc. for $C_{16}H_{12}N_3OCl$ (M+H), 298.0747; found, 298.0750.

Example 17: Synthesis and Characterization of 1-([1,1'-biphenyl]-3-yl)-4-aminopyrimidin-2(1H)-one (Bobcat222)

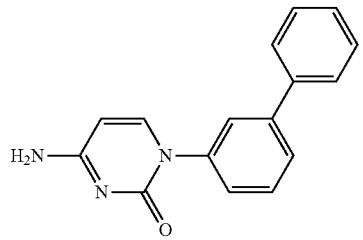 [SMILES: Nc1ccn(-c2cccc(-c3ccccc3)c2)c(=O)n1]

General procedure A was used to couple cytosine (250 mg, 2.25 mmol) and 3-biphenylboronic acid (1.5 eq.) to yield title compound. 88%. White powder. $R_f$=0.5 (10% MeOH in DCM; Seebach's Dip). $^1$H NMR (400 MHz, DMSO) δ 7.72 (m, 3H), 7.65 (m, 2H), 7.51 (m, 3H), 7.38 (m, 2H), 7.28 (d, 2H), 5.82 (d, 1H). $^{13}$C NMR (100 MHz, DMSO) δ 166.63, 155.37, 146.29, 142.35, 141.34, 139.77, 129.77, 129.45, 128.25, 127.27, 126.05, 125.96, 125.24. LCMS: $t_R$=4.21; m/z=264.1. HRMS m/z calc. for $C_{16}H_{13}N_3O$ (M+H), 264.1137; found, 264.1133.

Example 18: Cytosine Analogs Inhibited TET-Mediated Oxidation of Methylated DNA To determine whether cytosine analogs inhibited TET-mediated oxidation of methylated DNA, the amount of hydroxymethylcytosine in reactions containing TET enzyme alone or TET enzyme and a cytosine analog were determined using chemiluminescence ELISA assays.

Figure 1:
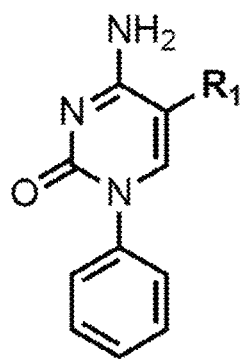
Figure 1:
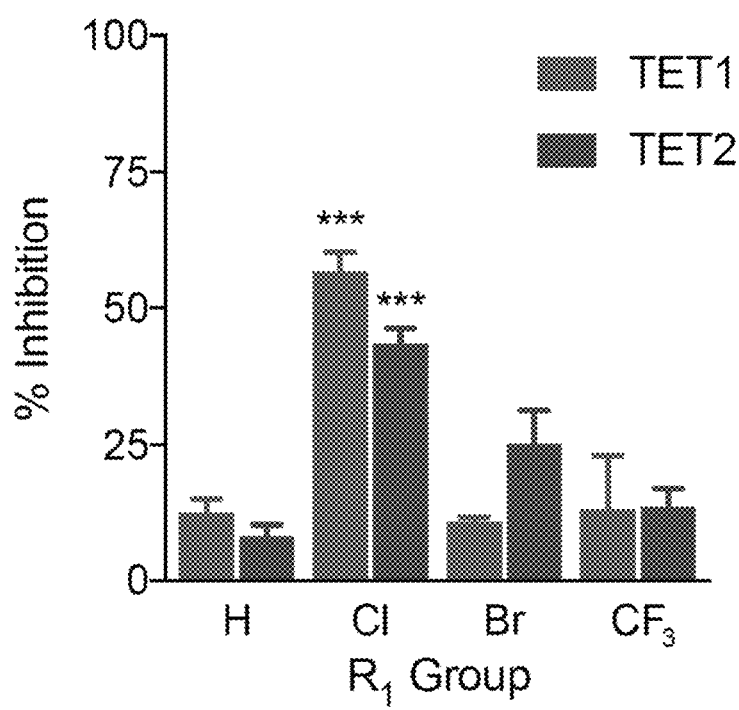

First, cytosine analogs with different methyl bioisosters at the $R_1$ position were tested for inhibition of TET1- or TET2-mediated oxidation of methylated DNA. Each compound was tested at 100 μM in the ELISA assay. Substitution of hydrogen, trifluoromethyl, and bromine at the $R_1$ position were insufficient to elicit significant inhibition (FIG. 1). However, the 5-chloro substitution was effective with 57% and 43% inhibition of TET1 and TET2, respectively (FIG. 1).

Figure 2A:
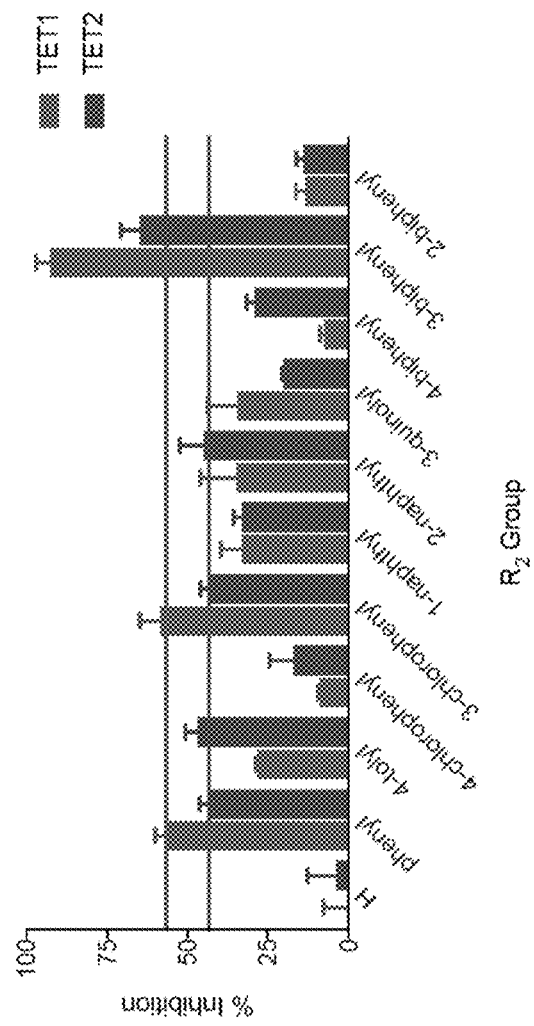
FIG. 2B is a graph showing results from testing 5-chloro substitution at the $R_1$ position. 5-chloro substitution at the $R_1$ position maintained the activity of 3-biphenyl substitution at the $R_2$ position for both TET1 (P<0.0001) and TET2 (P=0.0003). All data presented are N=3, error bars indicate+/−sem.
Figure 2A:
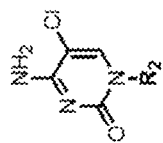
Figure 2B:
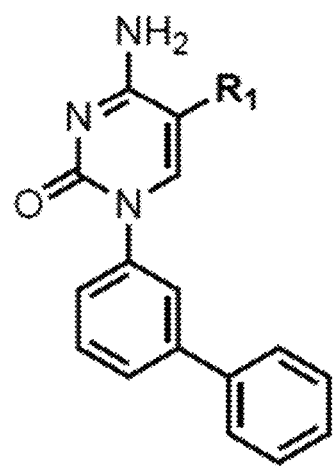
Figure 2B:
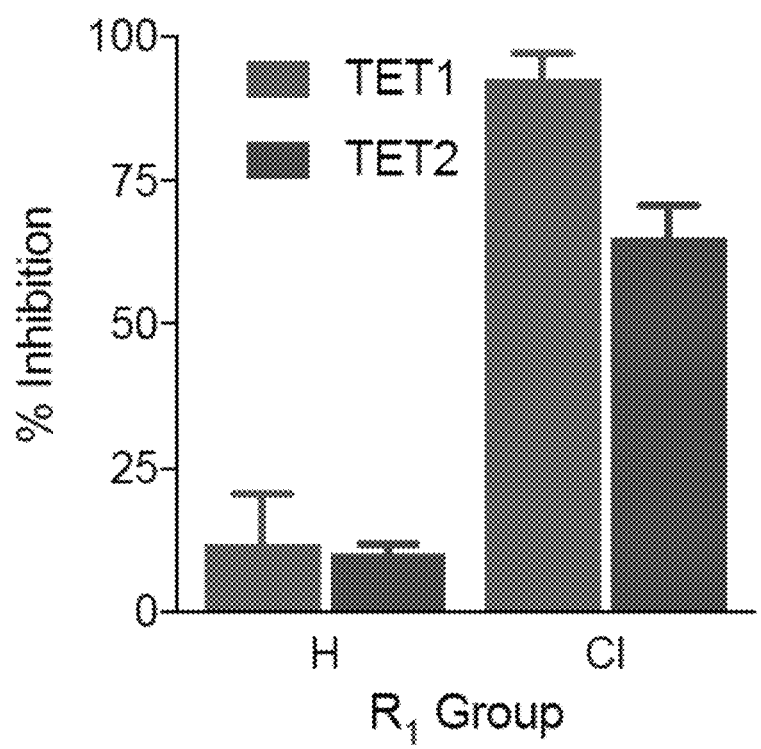

Next, cytosine analogs with different substituents at the $R_2$ position on the N1 of 5-chlorocytosine were tested for inhibitory activity against TET enzymes. These $R_2$ derivatives, which included tolyl, chlorophenyl, naphthyl, quinolyl, and biphenyl substitutions, performed with similar or worse potency to the original phenyl derivative (FIG. 2A). However, these results demonstrate that $R_2$ substitution is important for activity, as most aryl derivatives displayed significantly stronger inhibition than unsubstituted 5-chlorocytosine (FIG. 2A). Notably, compound Bobcat339, substituted at the $R_2$ position with 3-biphenyl, showed significantly enhanced activity at TET1 (P=0.002, two-way ANOVA) with comparable activity to the original phenyl derivative at TET2. This observed activity was also 5-chlorocytosine-dependent, and removal of the chlorine substituent significantly reduced activity at both TET1 (P<0.0001) and TET2 (P=0.0003) (FIG. 2B).

Figure 3A:
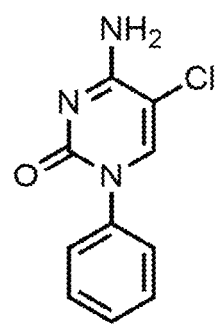
FIG. 3A is a graph showing results from testing different concentrations of Bobcat216 (KW1016) for TET inhibition.
Figure 3A:
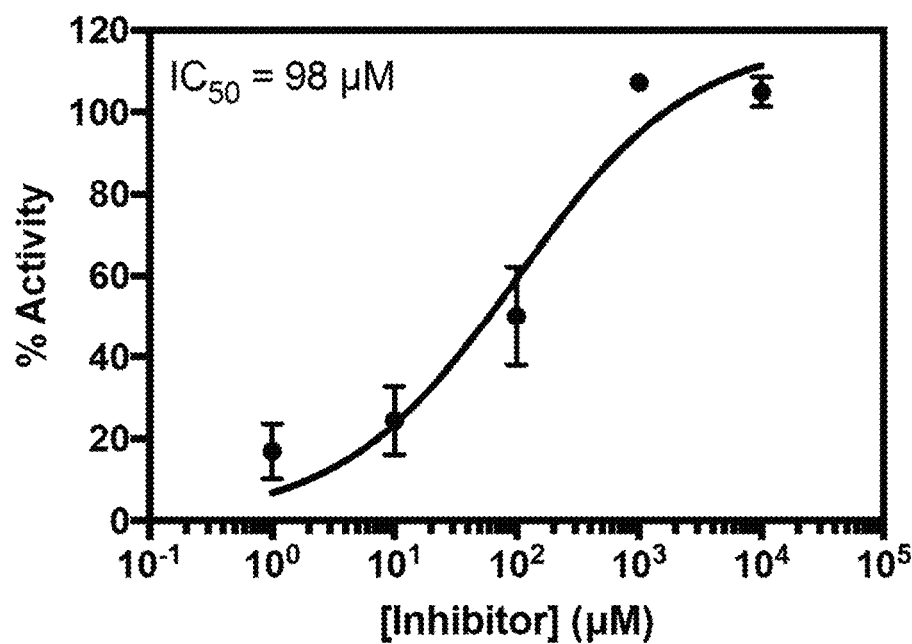
Figure 3B:
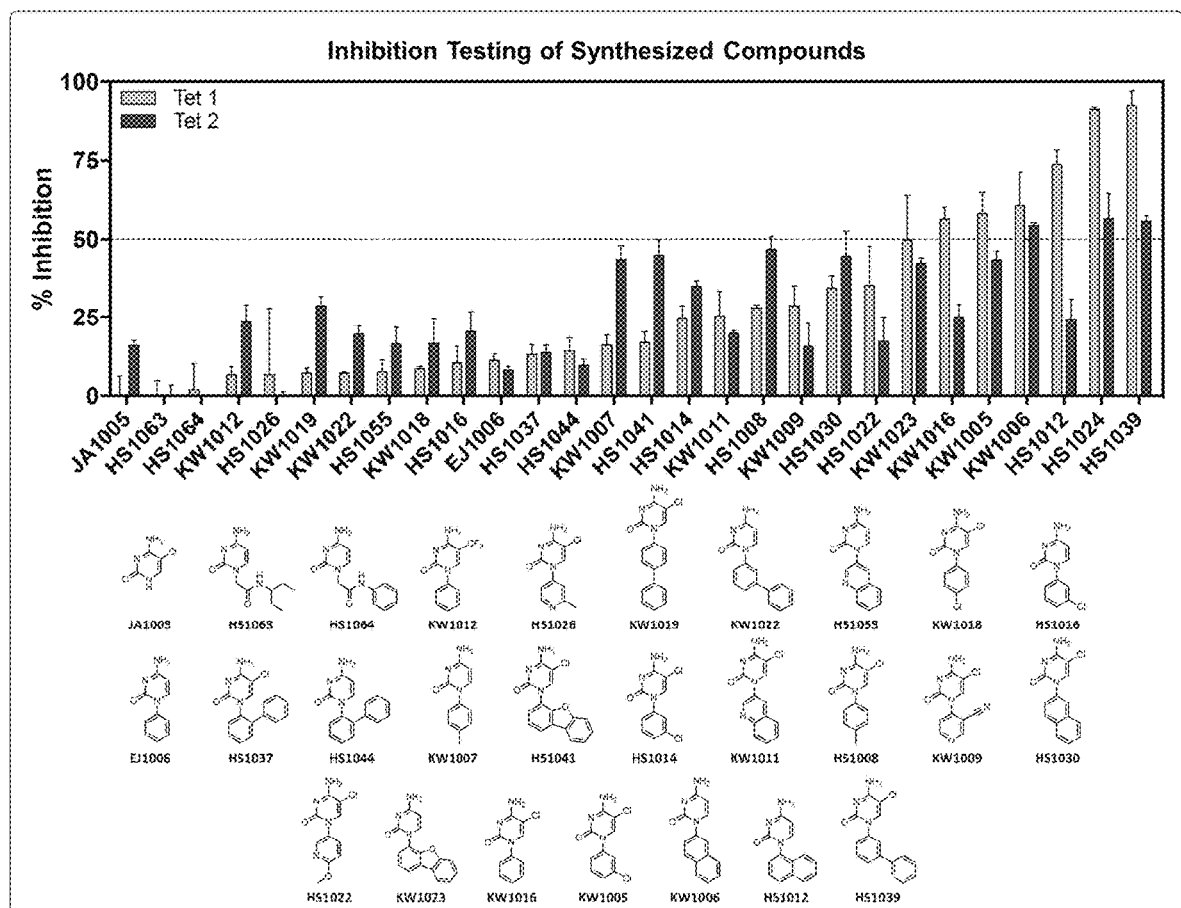
FIG. 3B is a graph showing results from testing different cytosine analogs for TET inhibition.

Next, the inhibitory activity of the original phenyl derivative Bobcat216 (KW1016) was tested at five different concentrations. The IC50 of Bobcat216 against TET2 was 98 μM (FIG. 3A). Each cytosine analog was tested for its inhibitory activity against TET1 and TET2 (FIG. 3B). HS1039, HS1024, and KW1006 were potent inhibitors of TET 1 and TET2 at 100 μM (FIG. 3B). HS1012 was a potent inhibitor of TET1, but not TET2 at 100 μM (FIG. 3B).

Taken together, these results demonstrate that cytosine analogs provided herein are potent inhibitors of oxidation of methylated DNA by TET1 and TET2 enzymes.

Chemiluminescence ELISA

Procedure adapted from manual (Bioscience; TET1: 50651, TET2: 50652). Prepare TBST buffer (1× TBS, pH 8.0, containing 0.05% Tween-20). Dilute 4.0× TET Assay Buffer (TAB) to 1.5× TAB and 1.0× TAB evenly with diluted water. Thaw and dilute (5.0 ng/μl for TET1 and 10 ng/μl for TET2) TET enzyme from kit with 1.0× TAB. Dilute primary antibody 100-fold with blocking buffer. Diluted secondary antibody 1000-fold with blocking buffer. Dilute DMSO inhibitor solutions with 1.0× TAB to wanted concentration (ensure solutions are 5% DMSO). To 96-well plate provided, add 200 μl TBST buffer to each well and incubate at room temperature for 15 min. Remove TBST buffer and add 20 μl 1.5× TAB, 10 μl inhibitor solution, 20 μl diluted TET to each well. For controls, add 10 μl 5% DMSO solution and 20 μl 1.0× TAB. Incubate at room temperature for 2 h. Remove reaction solution and wash 3× with TBST buffer (200, 200, and 100 μl). Add 100 μl blocking buffer 53 μl diluted primary antibody and shake at room temperature for 1 h. Remove diluted primary antibody and wash 3× with TBST buffer (200, 200, and 100 μl). Add 100 μl blocking buffer to each well and shake at room temperature for 10 min. Remove blocking buffer. Add 100 μl diluted secondary antibody. Shake at room temperature for 30 min. Remove diluted secondary antibody and wash 3× with TBST buffer (200, 200, and 100 μl). Add 100 μl blocking buffer to each well and shake at room temperature for 10 min. Remove blocking buffer. Combine horseradish peroxidase (HRP) substrate A and HRP substrate B at 1:1 ratio. Add 100 μl of HRP solution to each well. Immediately, read chemiluminescence (BioTek Synergy 2 plate reader).

Example 19: Cytosine Analog Bobcat339 Inhibited Removal but not Placement of Methyl Marks on DNA in Cells Since inhibiting active DNA methylation may counteract the potential therapeutic effects of inhibiting TET enzymes, Bobcat339 was evaluated for its desired role as a selective inhibitor of TET1 and TET2 using an inhibitory assay for DNMT3a. In brief, methylated DNA was examined by treating cultured HT22 cells with different concentrations of Bobcat339, extracting a DNA sample from the cultured HT22 cells, and measuring the hydroxymethylation (5-hmC) in the DNA sample using an ELISA assay.

Bobcat339 elicited a dose-response relationship for both TET1 (IC50=33 µM) and TET2 (IC50=73 µM), while failing to show substantial inhibition of DNMT3a at a concentration of 500 µM (FIG. 4).

These results demonstrate that cytosine analogs provided herein, such as Bobcat339, inhibit the removal, but not the placement of methyl marks on DNA.

Cell Culture

HT22 cells were provided by David Schubert at the Salk Institute (San Diego, Calif.). Cells were cultured in Dulbecco's Modified Eagle Medium (Life Technologies, Carlsbad, Calif.) supplemented with 10% FBS, 100 U/ml penicillin, and 100 µg/ml streptomycin (Life Technologies, Carlsbad, Calif.) at 37° C. and 5% CO2. HT22 cells were kept at 50-70% confluency and were passaged twice a week. Briefly, culture medium was removed and replaced by 0.05% trypsin (Life Technologies, Carlsbad, Calif.). The cells were incubated with trypsin for 5 minutes and 1.5× volume of culture medium was added to the cell-trypsin suspension. Finally, cells were added at a ratio of 1:10 to fresh culture medium in 35 mm dishes to be used for experiments. Cultured HT22 cells were treated with prepared solutions of Bobcat339 and Bobcat212. 22 µl of compound in DMSO was added to dishes containing 2.2 ml of cell medium, resulting in a 10 µM final concentration of inhibitor and an overall 1% DMSO concentration. Cells were incubated at 37° C. and 5% CO2 for 24 hours.

DNA Extraction

Procedure adapted from manual (Qiagen; 69504). Remove culture medium from dishes. Add 180 µl buffer ATL to each dish and scrape. Transfer liquid to 1.5 ml microcentrifuge tube. For each sample, add 20 µl proteinase K and immediately mix by pulse vortex. Incubate overnight at 56° C. After incubation, remove from incubator and vortex immediately for 15 seconds. Add 4 µl RNase A to each tube and vortex immediately. Let incubate for 2 mins at RT on bench top. To each sample, add 200 µl Buffer AL and mix thoroughly by vortexing. Add 200 µl ethanol (100%). Immediately mix by vortexing. Pipet each sample mixture into a DNeasy spin column placed in a 2 ml collection tube. Centrifuge at 6000× g (6000 rcf) for 1 minute. Discard the flow-through and collection tubes. Place each spin column in a new 2 ml collection tube, add 600 µl Buffer AW1, and centrifuge for 1 minute at 6,000×g. Discard the flow-through and collection tubes. Place the spin column in a new 2 ml collection tube, add 600 µl Buffer AW2, and centrifuge for 3 minutes at 18,213×g (18,213 rcf). Discard the flow-through and collection tubes, place spin column in new 2 ml collection tube, and centrifuge for another 3 minutes at 18,213×g (18,213 rcf). Place spin column into final full-description labeled 1.5 mL capped centrifuge tube. Add 22 µl DNase/RNase free water to each spin column as elution buffer and incubate on the benchtop at room temp for 15 minutes. Centrifuge for one minute at 6,000×g (6,000 rcf=6,000×g) and discard spin column. DNA concentrations were determined using a NanoDrop spectrophotometer and samples stored at −20° C.

MethylFlash Global DNA Hydroxymethylation (5-hmC) ELISA Easy Kit (Colorimetric)

Procedure adapted from manual (Epigentek: P-1032-48). Prepare Dilute Wash Buffer (1× Wash Buffer) by adding 13 ml of 10× Wash Buffer to 117 ml distilled water and adjusting pH 10 7.2-7.5. 100 µl of binding solution was to each well followed by 100 ng of extracted sample DNA or known standards, then incubated at 37° C. for 1 hour. Prepare 5-hmC Detection Complex Solution during the last 10 minutes of incubation by adding 1 µl hmAb, Signal Indicator, and Enhancer Solution per ml of Diluted WB (4-5 ml). After 1-hour incubation is complete, remove binding solution from each well and wash each well with 150 µl of diluted WB three times. After washing, add 50 µl of 5-hmC Detection Complex Solution to each well, mix by gently shaking the plate, then cover and incubate at room temperature for 50 minutes. After incubation, remove antibody solution from each well and wash each well with 150 µl each time for five times. After washing, add 100 µl of Developer Solution to each well column-wise so that replicates are developed at the same time. Incubate for 3-5 minutes or until the solution in the 1% PC wells turn dark blue. Stop the reaction by adding 100 µl of Stop Solution to each well column-wise. Incubate for 2 minutes, then read absorbance at 450 nm (BioTek Synergy 2 platereader).

Example 20: Calculated Differences in Binding Affinity of Cytosine Analogs Aligned with the Observed Differences in Enzyme Inhibition The inhibitory activity of Bobcat339 was not shared by its constitutional isomers, the 2-biphenyl and 4-biphenyl derivatives, and therefore the three-dimensional structures of these compounds in the TET active site were examined computationally.

The cytosine derivatives were docked into the active site of the TET2 crystal structure and a homology model of TET1 using the Molecular Operating Environment (MOE) software package. To generate the TET1 homology model, its primary protein sequence was aligned to that of the residues present in the published crystal structure of TET2 (FIG. 5A). Based on the binding orientation of 5mC, the cytosine derivatives were placed into the active site of the TET1 homology model. Then, allowing all bonds to rotate, a series of potential binding conformations was created. These conformations were next docked into both the TET1 and TET2 models, allowed to relax to a local energy minimum using the Amber10:EHT force field, and scored using the London ΔG algorithm.

The proposed binding mode of Bobcat339 for both isoenzymes situates the 5-chlorocytosine head group directly into the active site in a fashion that mimics the arrangement of 5mC, forming two base-pairing-like hydrogen bonds with the enzyme and placing the chlorine into the small pocket that typically accommodates the methyl substrate (FIG. 5B). Furthermore, the 3-biphenyl group is oriented at an angle to make hydrophobic contacts with the side wall of the binding pocket, which is disrupted when the biphenyl substitution pattern is altered. There is a high degree of homology between the active sites of both isoenzymes, and the calculated binding affinities of Bobcat339 are similar for TET1 (calc. $\Delta G_{Binding}$=−10.23 kcal/mol) and TET2 (calc. $\Delta G_{Binding}$=−10.08 kcal/mol). The 4-biphenyl derivative fails to take advantage of these interactions, while the 2-biphenyl derivative is forced into a different binding pose entirely due to what would be steric clashing with Tyr 1902 (FIG. 5C), leading to a decreased association with the active site for both the 4-biphenyl (calc. $\Delta\Delta G_{Binding}$=+0.99 kcal/mol) and the 2-biphenyl (calc. $\Delta\Delta G_{Binding}$=+0.52 kcal/mol) derivatives compared to Bobcat339 when docked into the TET1 model. Similar weaker binding affinities were also observed for the 4-biphenyl (calc. $\Delta\Delta G_{Binding}$=+0.37 kcal/mol) and the 2-biphenyl (calc. $\Delta\Delta G_{Binding}$=+0.72 kcal/mol) derivatives when docked into the TET2 model.

Taken together, these results demonstrate that the calculated differences in binding affinity aligned with the observed differences in enzyme inhibition elicited by these isomers.

KW1019 was docked to TET2 (FIG. 6A). Then, HS1039 and KW1019 were docked to TET 2 (FIG. 6B). The TET pocket appears to favor angled $R_2$ substituents in comparison to linear compounds, for instance, as can be observed for the greater inhibition associated with HS1039 over KW1019. Specifically, the model predicts higher binding scores for compounds that assume angles between the cytosine head-group and aryl tail-group of 90° to 180° due to the number of favorable contacts that can be made when the head-group is able to reside in a more "vertical" pose. The head-group of the linear compound however, must assume a more "tilted" pose, decreasing the number of preferred contacts with the pocket.

HS1039 and HS1041 were docked to TET2 (FIG. 6C). HS1039 and HS1041 showed distinct inhibitory preference for either TET1 or TET2. Although these compounds are similar in size and shape, HS1039 exhibited greater inhibition for TET1, and HS1041 for TET2. This difference in specificity may be due to a preference of TET2 for binding a planar molecule. Although HS1039 may assume a planar conformation, the energy cost associated with fixing the molecule in a position with more steric strain is of consequence.

Computational analyses suggested that the TET2 pocket may contain more available space to accommodate larger structures than contained within the first generation library of compounds. Predicted binding energies were higher for molecules with larger R2 groups due to the greater number of favorable contacts being made (FIG. 6D).

Taken together, these results demonstrate that TET2 may prefer binding a planar $R_2$ moiety, which indicates that compounds with rotatable bonds must assume conformations with higher degrees of steric strain and pay the energy cost. In addition, these results demonstrate that larger compounds may bind more favorably with TET2.

TET Enzyme Computational Models

A solved crystal structure of human TET2 bound to DNA (PDB: 4NM6) was used in the Molecular Operating Environment (MOE) software for all computational analyses. A homology model of human TET1 was then produced by aligning its relevant primary sequence with that of TET2, and then substituting the linear amino acid sequence with an induced fit around the N-oxalylglycine-Fe-methylated dsDNA complex using the Amber 10 EHT force field in the MOE software package. TET2 was crystalized, bound to dsDNA, with N-oxalylglycine, a pan inhibitor of KG-dependent dioxygenase. For both TET1 and TET2 models the nitrogen in N-oxalylglycine, which binds to the KG cofactor site and chelates the catalytic Fe center, was then converted to an $sp^3$ hybridized carbon to produce KG. Then, the dsDNA was removed from the model and the bound 5mC in the active site was used as the starting pose for all cytosine-based inhibitors.

Inhibitor Docking

Analogs of 5-chlorocytosine were generated using the molecule builder feature in the MOE software, and based on the binding position of 5mC in the crystal structure. Each compound was first allowed to minimize to its lowest energy conformation within the pocket in the Amber 10 EHT force field, while all other protein atoms were fixed. Then, a systematic conformational search was run for each compound, and each rotatable bond in R2 was rotated to generate a library of low energy conformers. Each member of this library was then docked using the docking function in MOE and scored using the London $\Delta G$ function to obtain a score for free energy of binding. No placement methodology was used, but the induced fit function was employed as the refinement methodology, while allowing protein atoms of residues within 4.5 Å of the inhibitor free to minimize torsional strain and maximize interactions.

Example 21: Design and Development of Cytosine-Based TET Enzyme Inhibitors

The design and development of potent inhibitors of the TET enzymes utilized the solved crystal structure of human TET 2 (FIG. 7A). The structure, which shows the TET 2 enzyme bound to methylated double stranded DNA (dsDNA), reveals how the enzyme isolates and recognizes 5mC by orientating its methyl substituent proximal to the oxidative Fe center. Several critical hydrogen bonds are formed for enzymatic recognition of 5mC. Asn1387 accepts a hydrogen bond from N7 and His1904 donates a hydrogen bond to N3 of the 5mC ring (FIG. 7A-7B). Mutating either residue leads to the loss of enzymatic function and reduced binding affinities to methylated DNA. Therefore, these contacts were maintained in the de novo design of competitive inhibitors based on cytosine. The deoxyribose also makes positive contacts with the active site in the form of a water-mediated hydrogen bond between the hydrofuran oxygen and Arg1261, a critical residue that also binds alpha-ketoglutarate. The methyl substituent on cytosine increased binding affinity to TET2, however, installing a methyl group into the design would likely produce a competitive substrate rather than an inhibitor. Thus, the design and development of cytosine-based TET enzyme inhibitors included identifying a suitable bioisostere for the methyl at the 5 position.

Example 22: DNA Methylation Analysis

Whole genome bisulfite sequencing in HT22 cells was performed. A significant change in global CpG methylation was observed (FIG. 8). Generally, the genome was broken into windows each containing 25 CpGs, and an analysis was performed to determine differentially methylated regions. A thousand such regions were observed, most of which are hypermethylated. Such regions were observed to be concentrated at promoters (and several markers of active promoters), and significantly concentrated at promoters of experience regulated genes (ERGs) as observed with Tet1 downregulation and Tet2 knockout. Additionally, the differentially methylated regions (DMRs) were highly associated with DMRs detected for those Tet gene deficient cells/tissue.

Cell Culture Protocol

HT-22 cells were provided by David Schubert at the Salk Institute (San Diego, Calif.). Cells were cultured in Dulbecco's Modified Eagle Medium (Life Technologies, Carlsbad, Calif.) supplemented with 10% FBS, 100 U/ml penicillin, and 100 µg/ml streptomycin (Life Technologies, Carlsbad, Calif.) at 37° C. and 5% CO2. HT-22 cells were kept at 50-70% confluency and were passaged twice a week. Briefly, culture medium was removed and replaced by 0.05% trypsin (Life Technologies, Carlsbad, Calif.). The cells were incubated with trypsin for 5 minutes and 1.5× volume of culture medium was added to the cell-trypsin suspension. Finally, cells were added at a ratio of 1:10 to fresh culture medium in 35 mm dishes.

Treatment with Bobcat339

Cultured HT-22 cells were treated with Bobcat339. 22 µl of compound solution at each concentration was added to dishes containing 2.2 ml of cell medium, resulting in the following in-well concentrations of each compound in 1% DMSO at 10 µM. Cell dishes were incubated at 37° C. and 5% $CO_2$ for 24 hours before observation. All dishes were then snap-frozen at −80° C. prior to DNA extraction.

Whole Genome Bisulfite Sequencing

Cells were lysed and gDNA was extracted (Qiagen, DNeasy), bisulfite converted (Accel-NGS Methyl-Seq DNA Library, Swift), and sequenced (Hudson Alpha Discovery) on the Illumina platform (HiSeq_X10, paired end, 150 bp, 500 million reads per sample). Reads were QC'd by FastQC (v0.11.5), filtered by quality (average quality score <20), Illumina adapters removed, and sequencing primers trimmed using Trim_Galore! (v0.4.5) according to the Swift kit specifications. The filtered and trimmed reads were then mapped to the mouse genome (mm10), deduplicated, and CpG methylation levels extracted using Bismark (v0.19.0). Altered CpG methylation was determined by dividing the mouse genome into ~850,000 windows, each containing 25 CpG sites. DMRs were determined using the EdgeR (for/rev) algorithm available in the Seqmonk (v1.44.0) software package, where significant differences between genotypes were determined by an FDR<0.05. H2A.Z binding sites were determined using previously published datasets,[1] as well as for determining active hippocampal promoters and enhancers[2] and learning-associated genes.[3] Prior to bisulfite conversion, samples were spiked with unmethylated Lambda DNA. Reads were also mapped using Bismark to the Lambda genome to confirm cytosine hydrolysis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. All references, patents and patent applications disclosed herein are incorporated by reference with respect to the subject matter for which each is cited, which in some cases may encompass the entirety of the document. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A composition comprising a cytosine analog of forma I

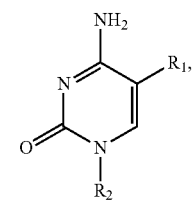

or a pharmaceutically acceptable salt thereof,
wherein $R_1$ is independently selected from the group consisting of hydrogen, halogen, and an unsubstituted methyl, and
wherein $R_2$ is selected from the group consisting of an optionally substituted phenyl or pyridyl group, and
wherein the cytosine analog is in an amount effective to inhibit a Ten-eleven translocation (TET) enzyme.

2. The composition of claim 1, wherein $R_1$ is hydrogen.

3. The composition of claim 1, wherein $R_1$ is halogen.

4. The composition of claim 1, wherein $R_1$ is methyl.

5. The composition of claim 3, wherein $R_1$ is Cl.

6. The composition of claim 1, wherein $R_2$ is optionally substituted phenyl.

7. The composition of claim 6, wherein the optionally substituted phenyl is substituted with halogen, optionally substituted $C_{1-6}$alkyl, or phenyl.

8. The composition of claim 6, wherein $R_2$ is unsubstituted phenyl, 4-chlorophenyl, 3-chlorophenyl, 2-biphenyl, 3-biphenyl, 4-biphenyl, or 4-methylphenyl.

9. The composition of claim 1, wherein $R_2$ is optionally substituted pyridyl.

10. The composition of claim 1, wherein the cytosine analog of formula I is selected from the group consisting of:

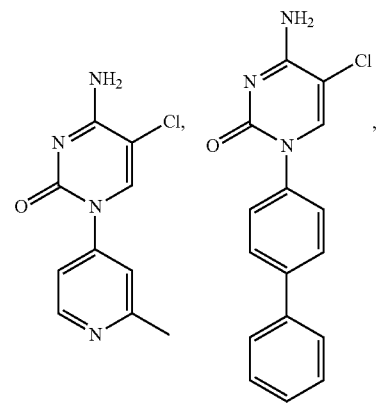

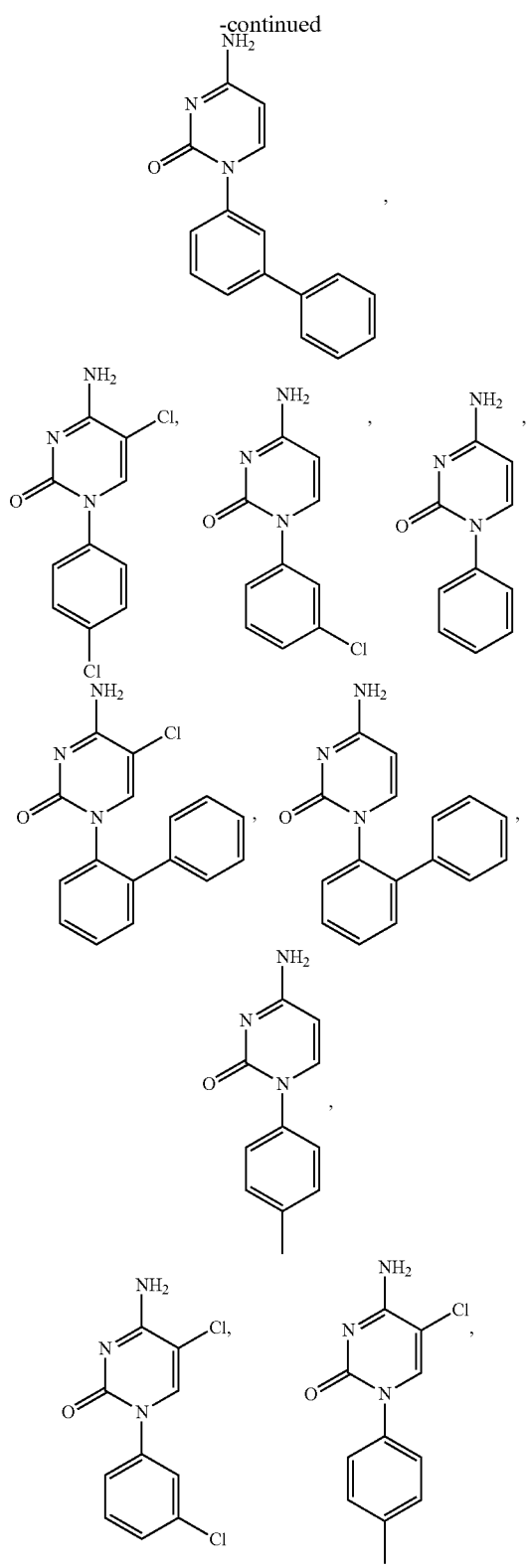
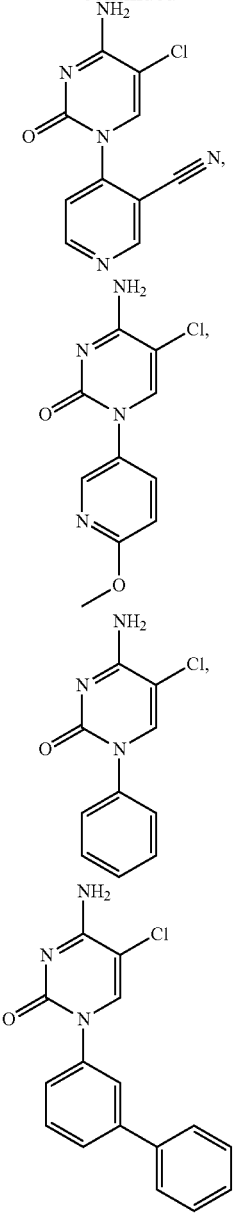
and a pharmaceutically acceptable salt of one of the aforementioned compounds.
11. A method for inhibiting a Ten-eleven translocation (TET) enzyme, the method comprising contacting the composition of claim 1 with the TET enzyme.
12. The method of claim 11, wherein the TET enzyme is TET1, TET2 or TET3.
13. The method of claim 11, wherein the contacting occurs in vitro or in vivo.
* * * * *